United States Patent [19]

Matzuk

[11] 4,106,346
[45] Aug. 15, 1978

[54] GREY-LEVEL ULTRASONIC IMAGING

[76] Inventor: Terrance Matzuk, 154 Eileen Dr., Pittsburgh, Pa. 15214

[21] Appl. No.: 780,277

[22] Filed: Mar. 23, 1977

[51] Int. Cl.² .............................................. G01N 29/04
[52] U.S. Cl. ........................................ 73/614; 73/620; 73/627; 128/2 V
[58] Field of Search ................... 73/67.8 S, 67.9, 609, 73/610, 614, 620; 340/5 MP; 128/2 V; 315/30; 358/112

[56] References Cited

U.S. PATENT DOCUMENTS

| 3,548,641 | 12/1970 | Michell | 73/67.9 |
| 3,856,985 | 12/1974 | Yokoi et al. | 73/67.8 S |
| 3,902,476 | 9/1975 | Hileman | 128/2 V |
| 3,918,297 | 11/1975 | Rocha | 73/67.7 |

OTHER PUBLICATIONS

J. Karman et al, Displaying Gray-Scale Images on Bistable Storage Tubes, Electronics, Nov. 22, 1973, pp. 132 & 133.

Primary Examiner—Richard C. Queisser
Assistant Examiner—John P. Beauchamp
Attorney, Agent, or Firm—Arnold B. Silverman

[57] ABSTRACT

Apparatus and method for grey-level ultrasonic imaging employing a storage oscilloscope. In medical diagnostic uses, a patient originated ultrasonically reflected wave is converted into an electrical signal which is so modulated as to result in grey-level type display on a bistable type storage oscilloscope or otherwise recorded or displayed. This display may be directly produced and immediately viewed.

47 Claims, 75 Drawing Figures

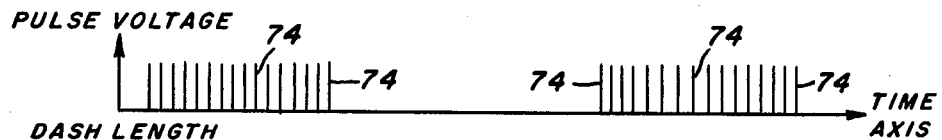
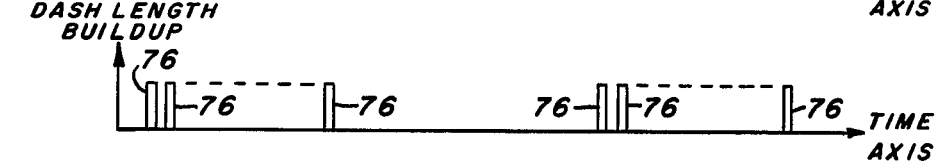
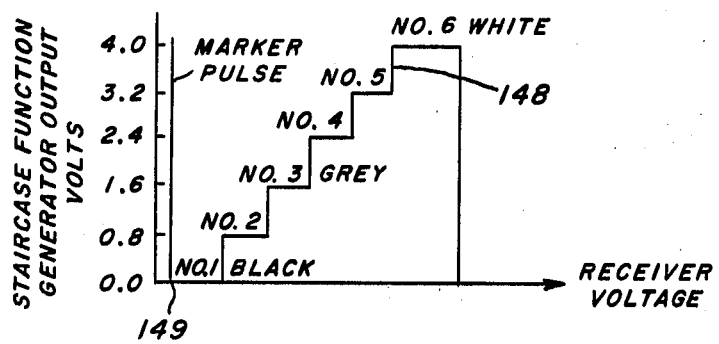
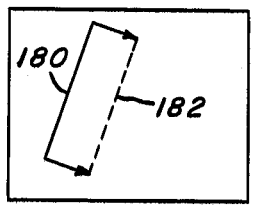
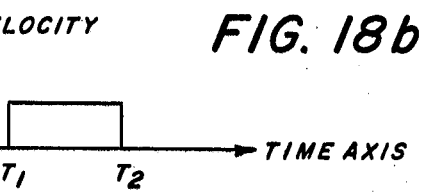
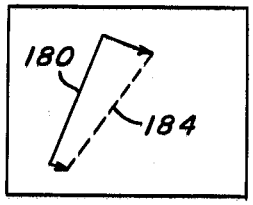
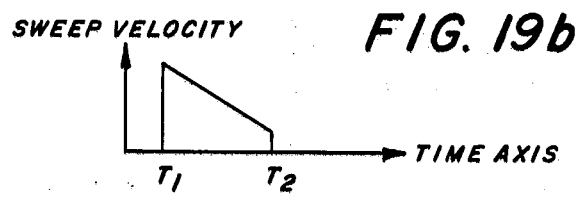
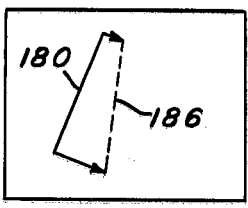
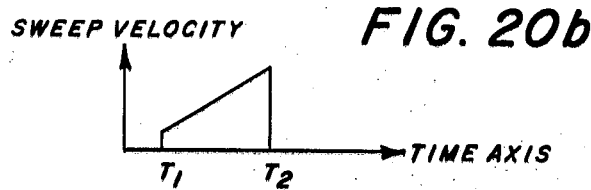

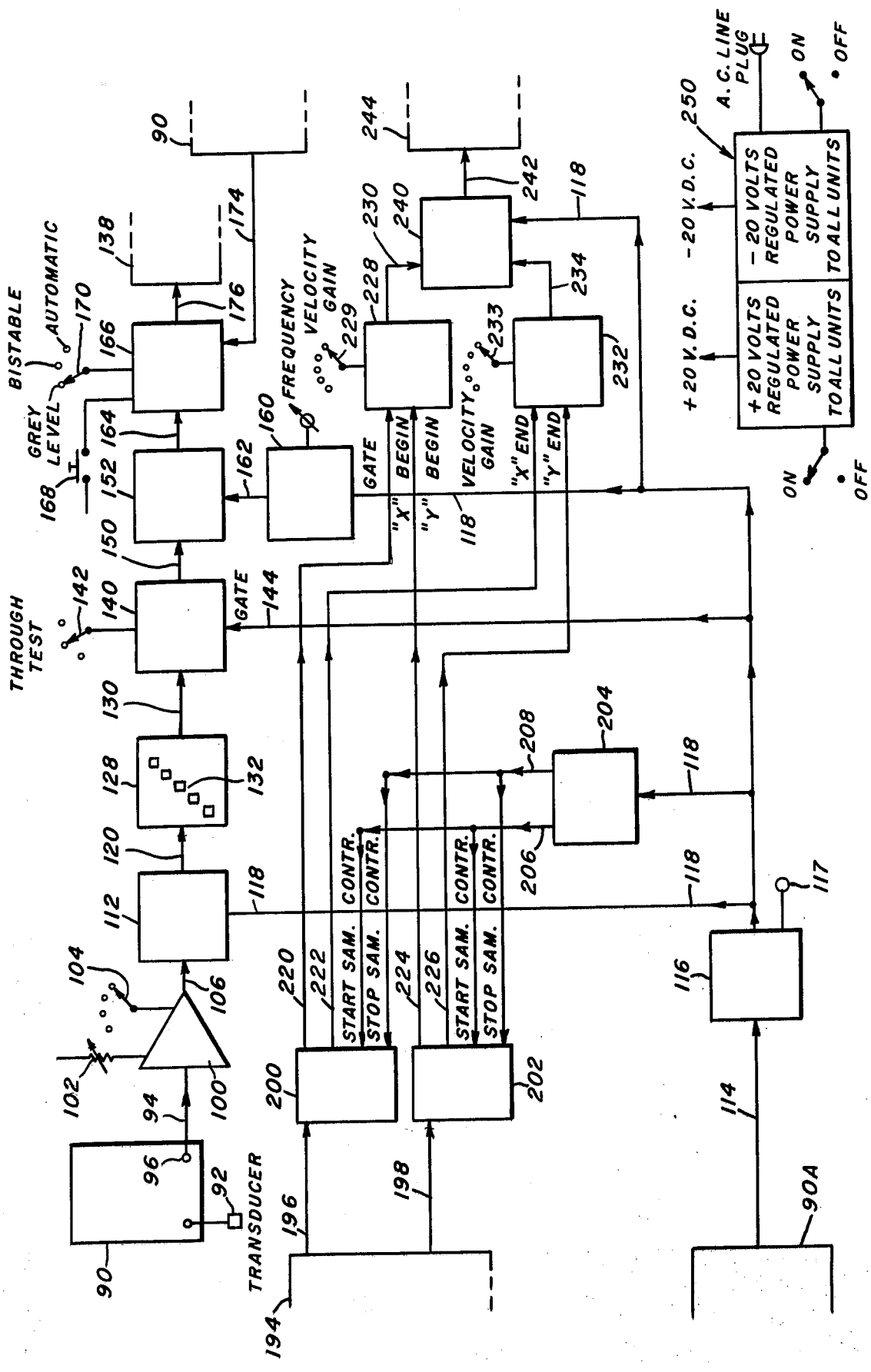

FIG. 22a
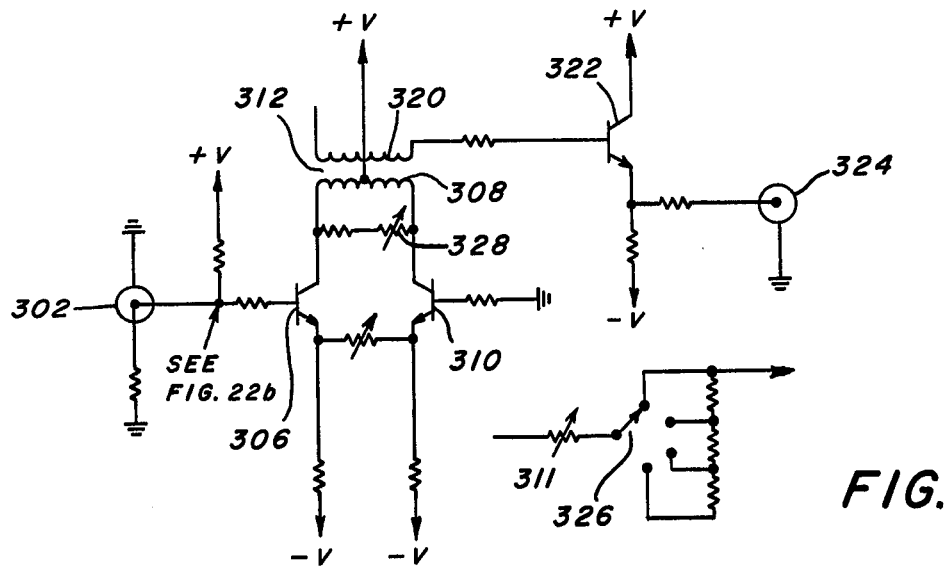
FIG. 22c
FIG. 22b
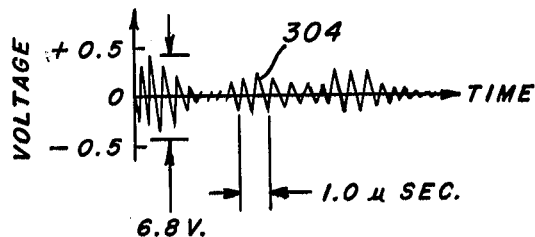
FIG. 27
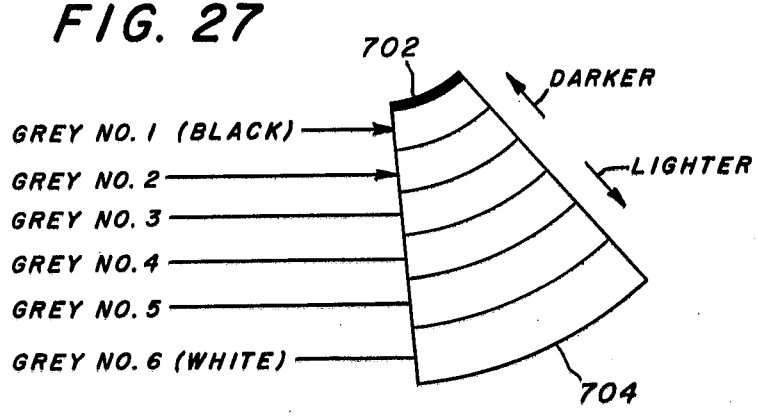

FIG. 23a
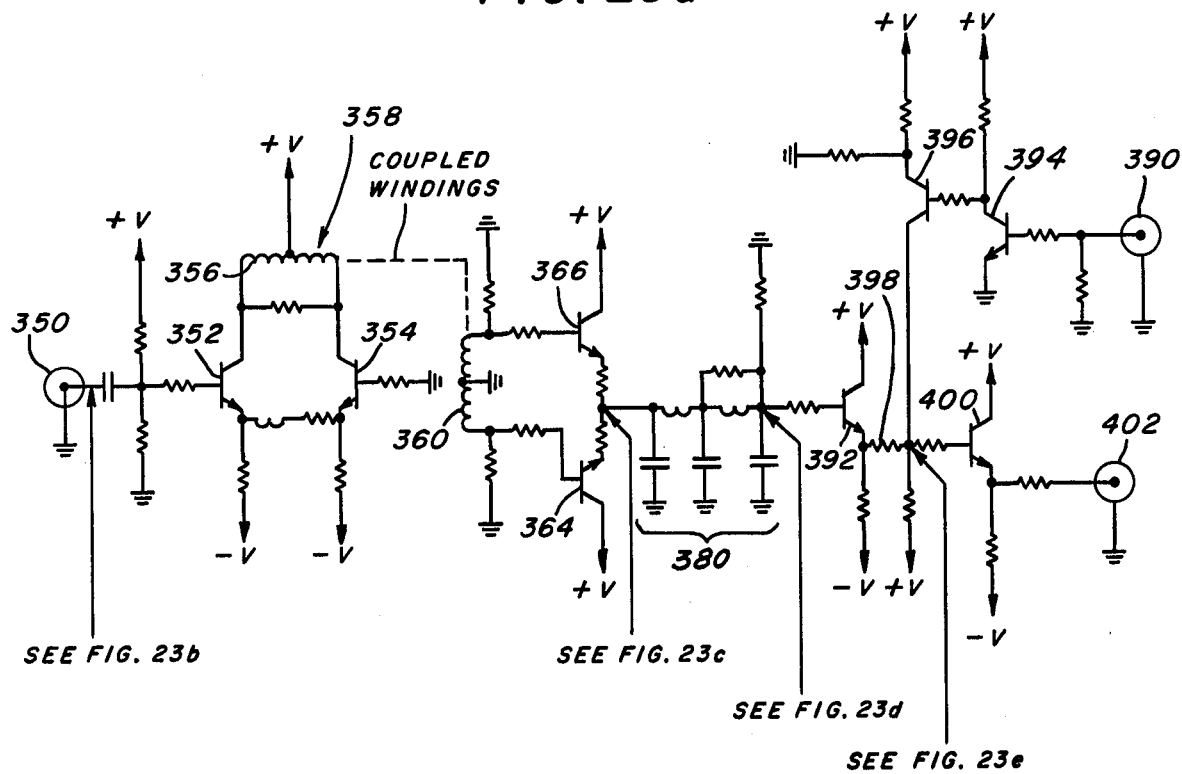
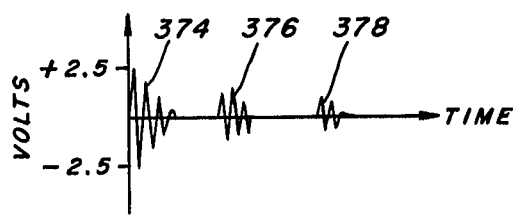
FIG. 23b
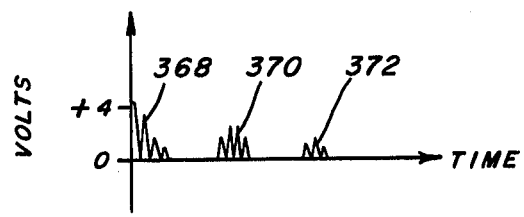
FIG. 23c
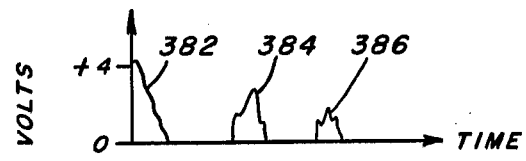
FIG. 23d
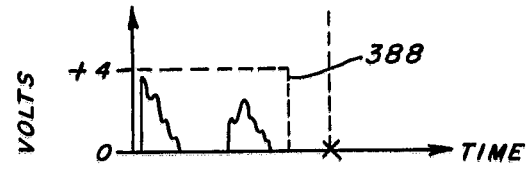
FIG. 23e

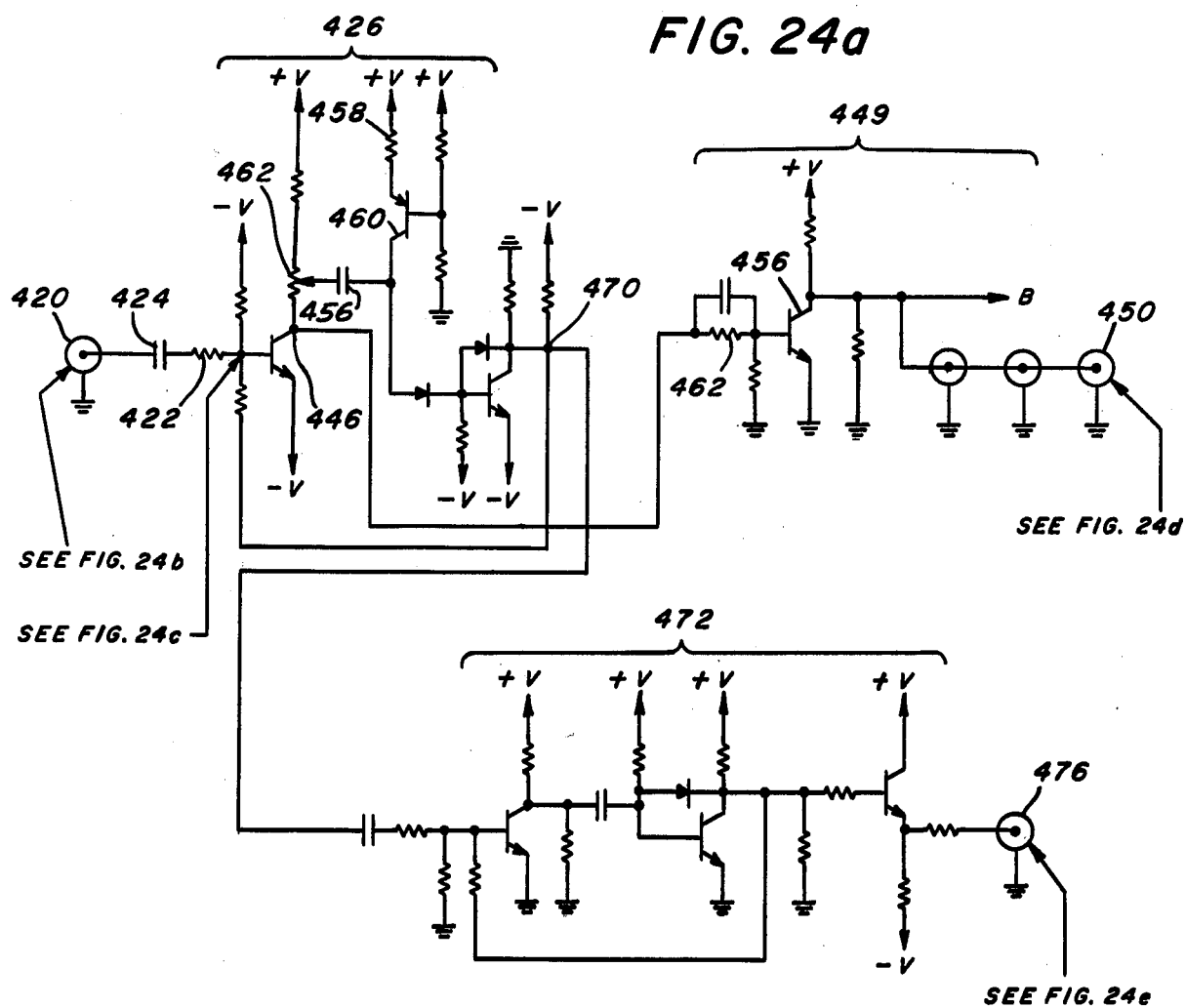
FIG. 24a
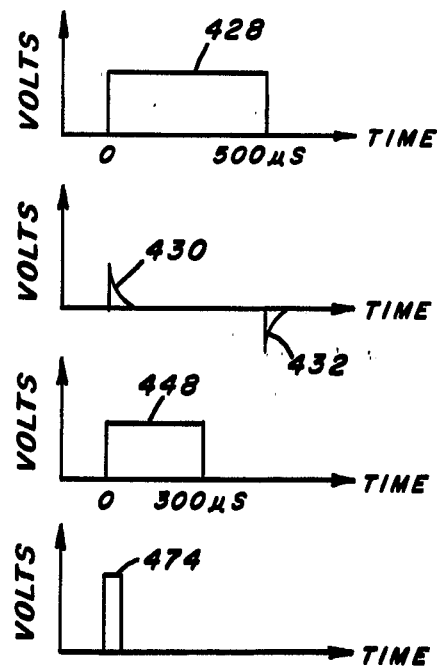
FIG. 24b
FIG. 24c
FIG. 24d
FIG. 24e

FIG. 25a
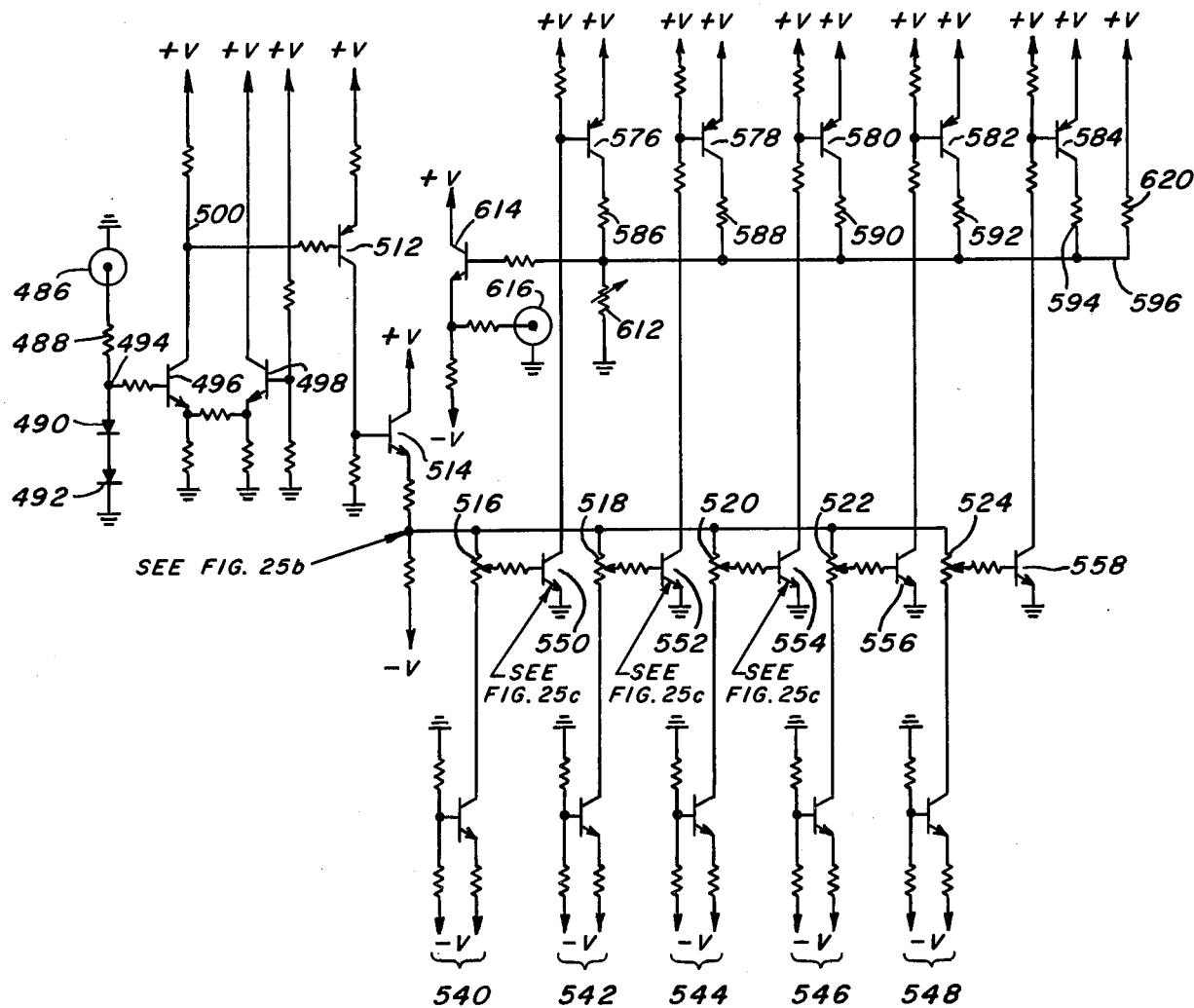
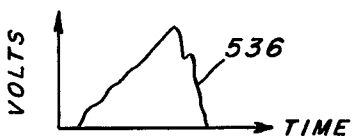
FIG. 25b
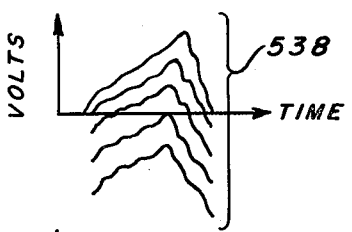
FIG. 25c
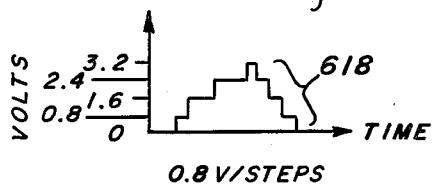
FIG. 25d

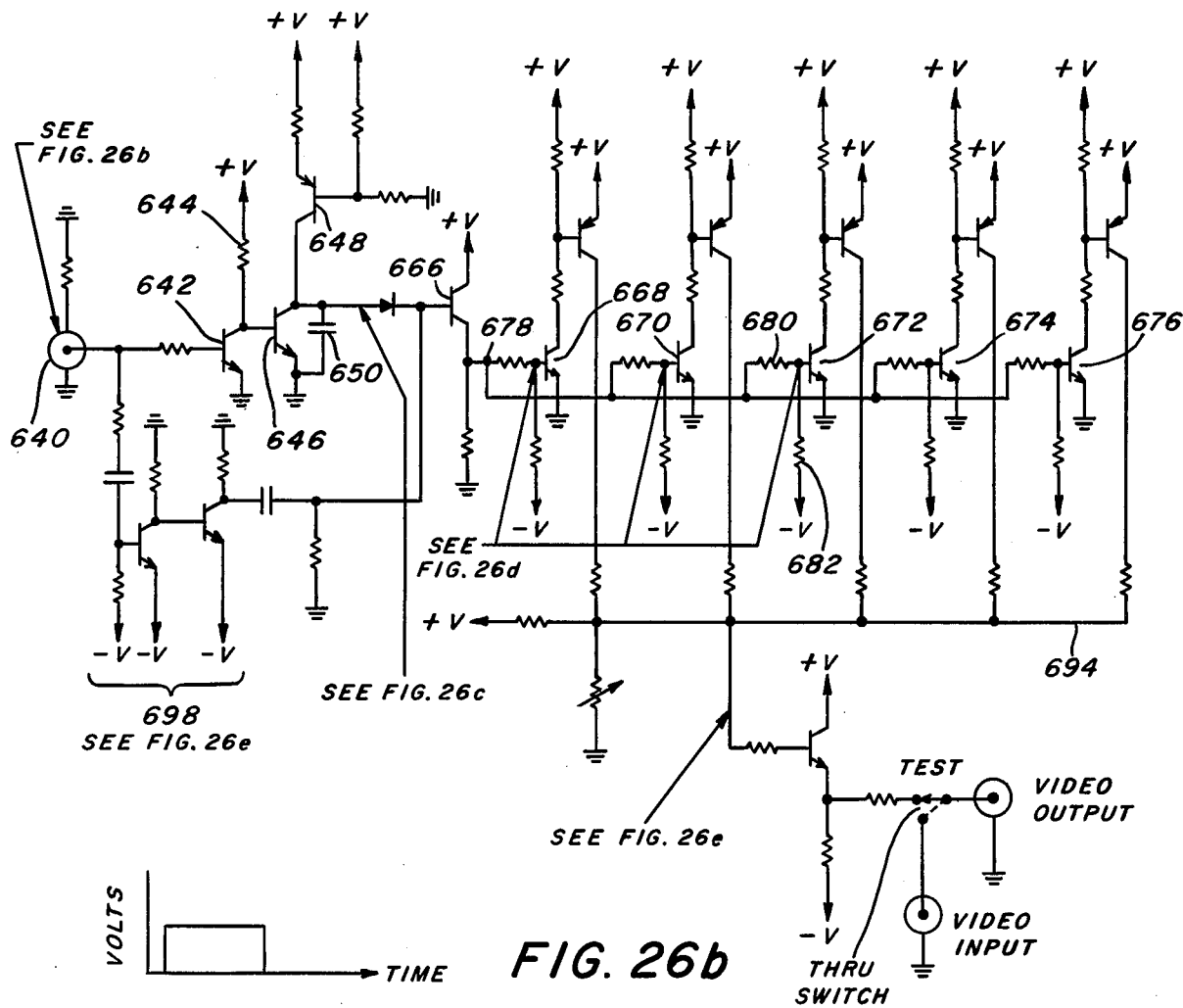
FIG. 26a
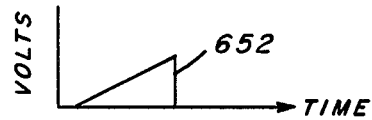
FIG. 26b
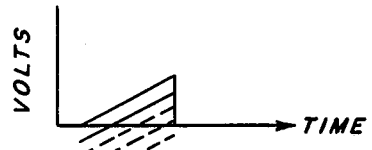
FIG. 26c
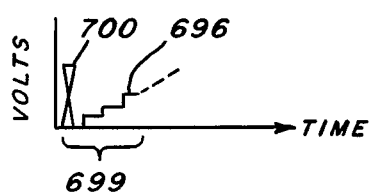
FIG. 26d
FIG. 26e FIG. 28a
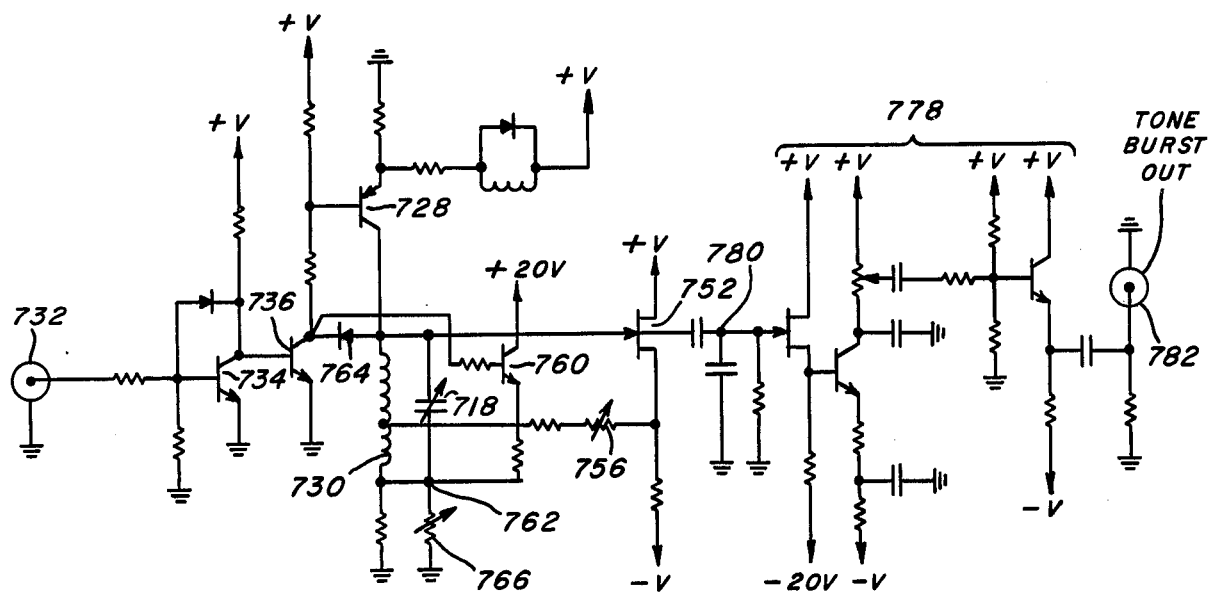
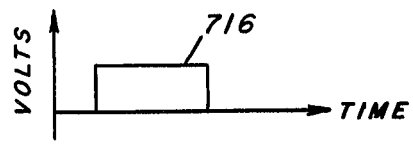
FIG. 28b
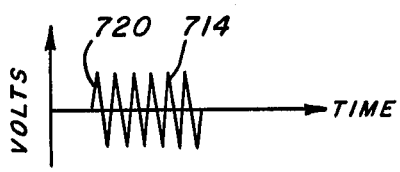
FIG. 28c
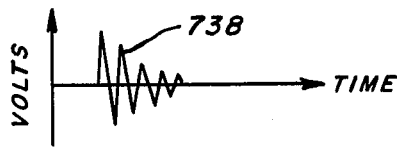
FIG. 28d
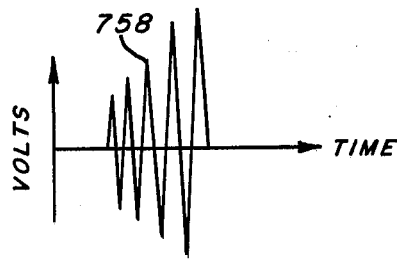
FIG. 28e FIG. 29a
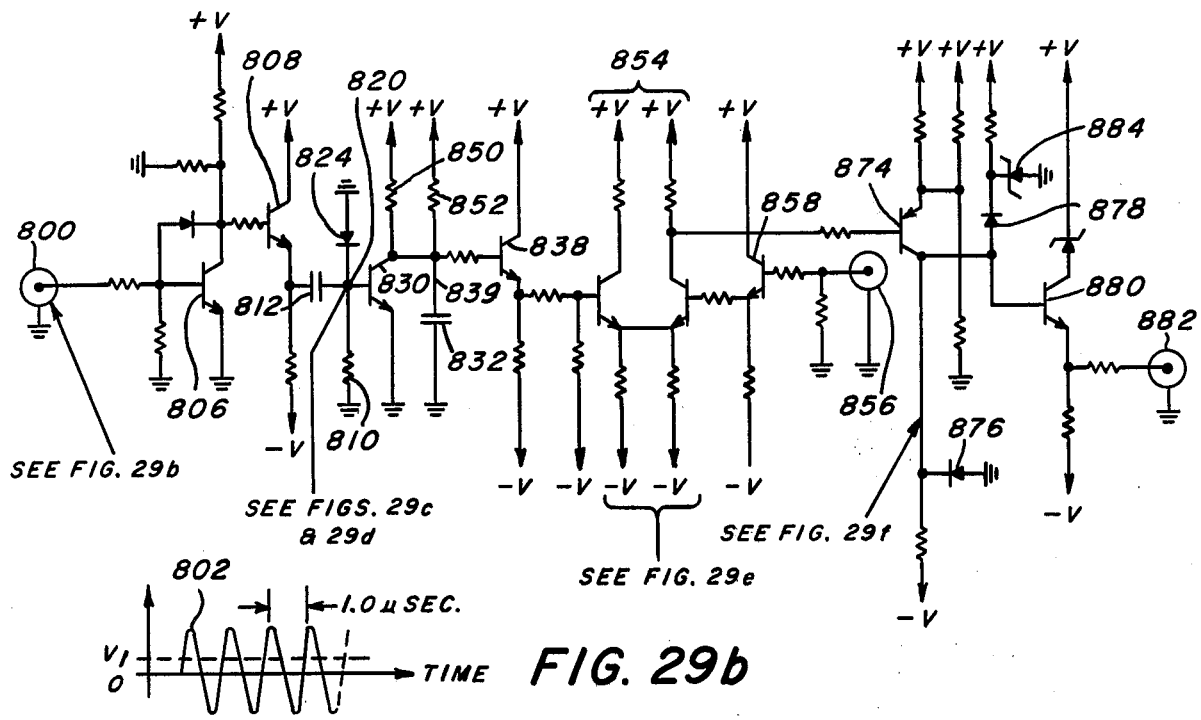
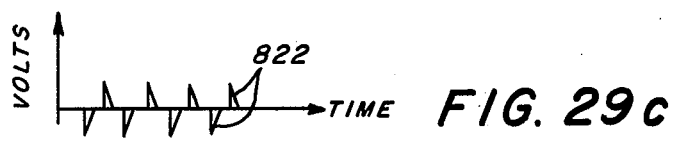
FIG. 29b
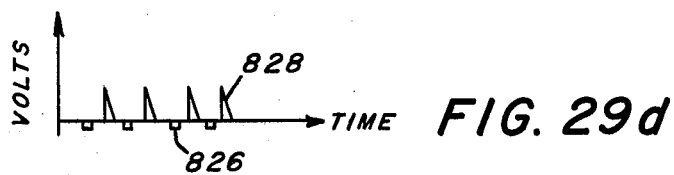
FIG. 29c
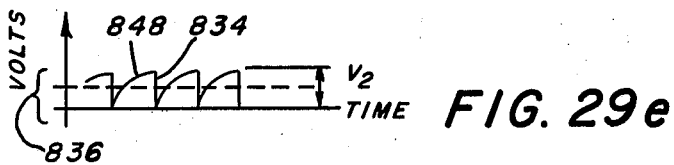
FIG. 29d
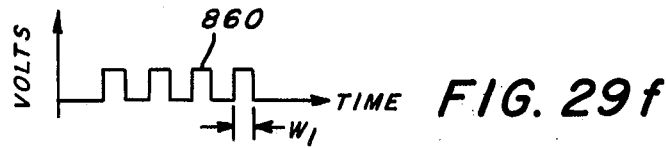
FIG. 29e
FIG. 29f FIG. 31a
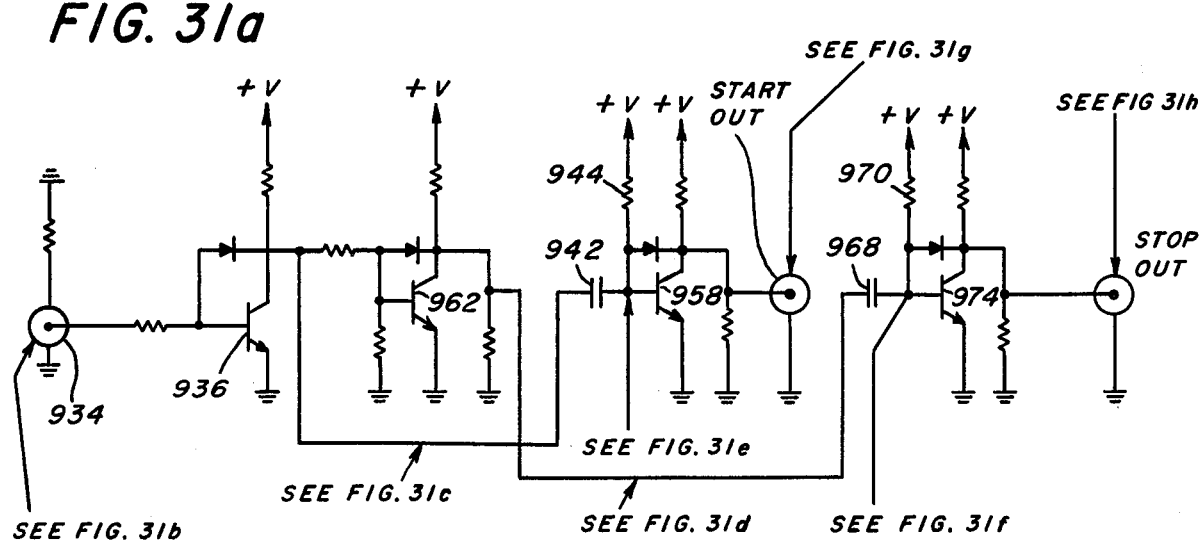
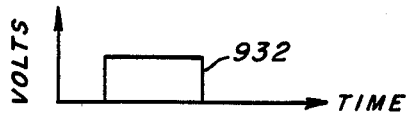
FIG. 31b
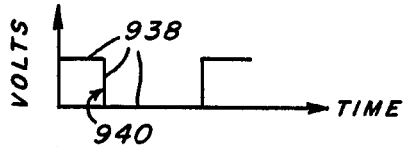
FIG. 31c
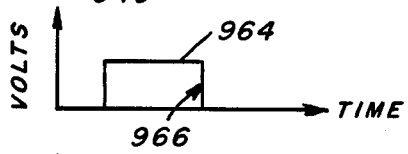
FIG. 31d
FIG. 31e
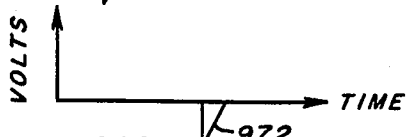
FIG. 31f
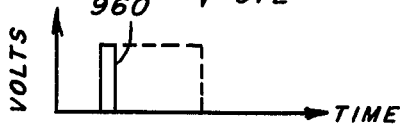
FIG. 31g
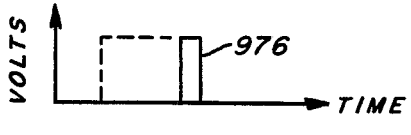
FIG. 31h

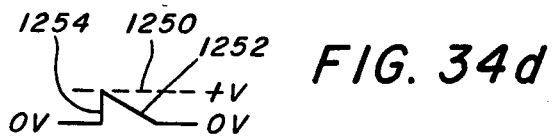
FIG. 34d
FIG. 34c
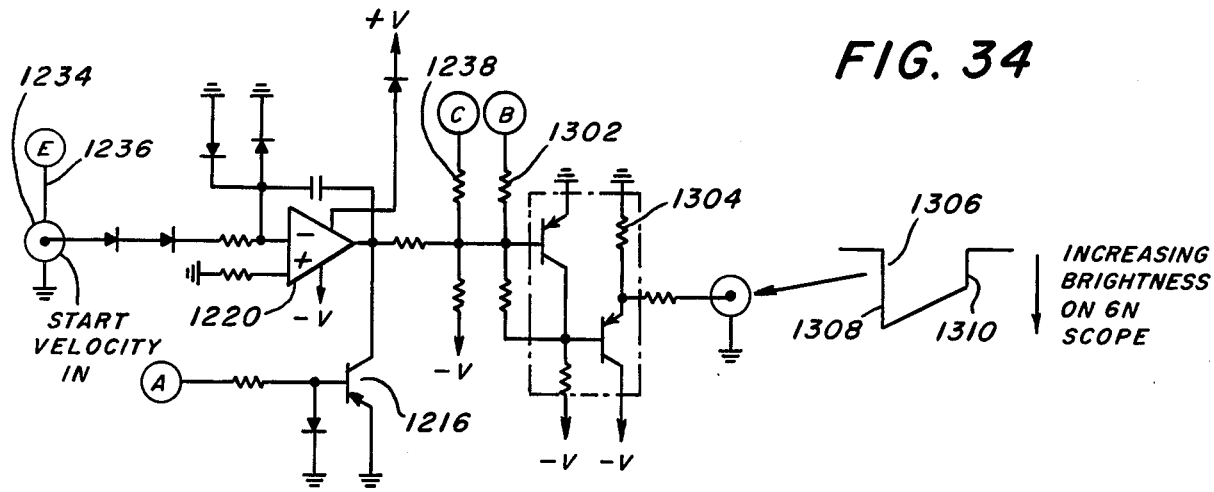
FIG. 34
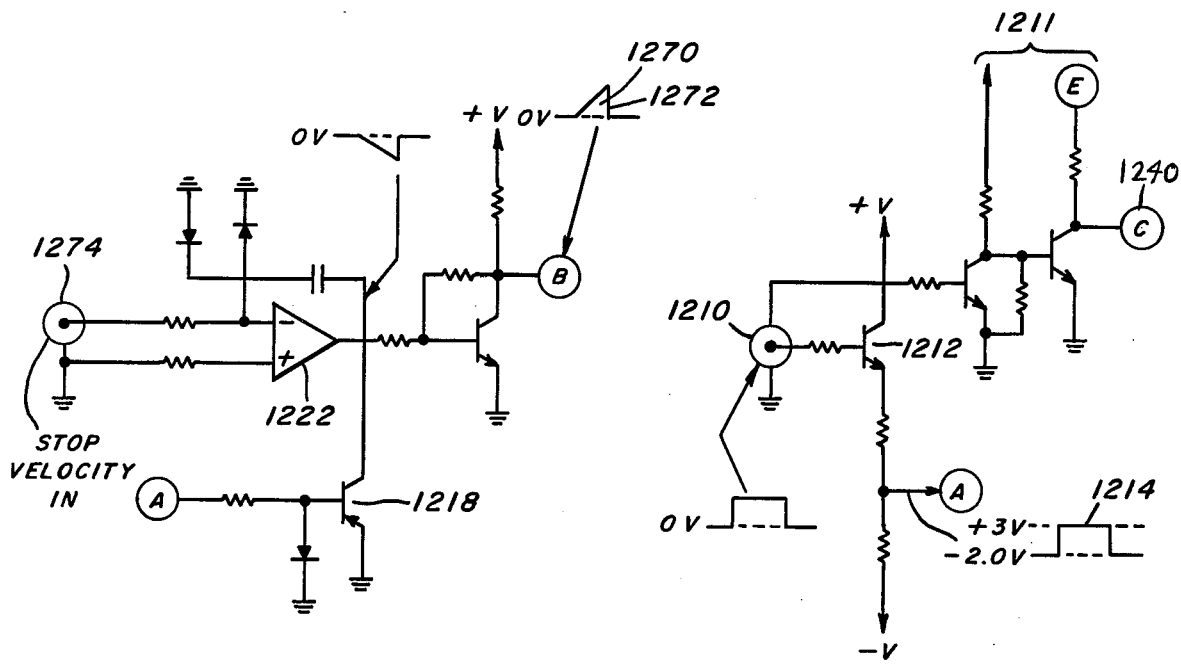
FIG. 34b
FIG. 34a

GREY-LEVEL ULTRASONIC IMAGING

BACKGROUND OF THE INVENTION

1. Field of the Invention

This invention relates to grey-level, ultrasonic imaging and, more specifically, provides a system and method of establishing grey-level, ultrasonic images while employing conventional ultrasonic signal generating means and a bistable storage oscilloscope.

2. Description of the Prior Art

It has been known to employ ultrasonic B-scan type equipment in diagnostic medical procedures as well as in other uses. In such an arrangement, in connection with use on a human or animal patient or specimen, an ultrasonic pulse is generated by the piece of ultrasonic testing equipment. The ultrasonic wave impinges upon the patient, and a number of reflected waves are sent back into the instrument. In a conventional system, the signal is then converted into an electrical signal which is visually displayed upon a bistable storage oscilloscope. In the bistable storage oscilloscope, the amplitude of the voltage of the electrical signal, which is related to the ultrasonic reflected wave, is divided at a certain threshold level. The voltage wave portions which are under that threshold level appear on the storage oscilloscope screen as black. The voltage wave portions which are higher than the threshold level are displayed as white dots or bars. In this fashion, a picture of the portion of the patient or specimen examined is displayed in what amounts to a "go-no go" approach. This approach to the use of ultrasonics has severe limitations in that establishing the decision of threshold voltage level is somewhat arbitrary, and the use of a bistable system precludes the visualization of "fine structure" information regarding the patient or specimen. Even in situations where a more complex "decision threshold" is established, such as through use of time derivative functions of the reflected signals, the basic inability to show refined pictures of the patient or specimen remains a problem.

Efforts have been made to refine the picture presented by conventional oscilloscopes, as well as by bistable storage oscilloscopes.

U.S. Pat. No. 3,902,476 discloses pulse width modulation as applied to medical diagnostic ultrasonics. In this disclosure, the connected dot-pattern displays are purposely elongated into overlapping or connected dashes in an effort to improve visual continuity in electronic graphic displays and to improve the visually apparent frequency response in such displays. Primary emphasis is directed toward improving bistable displays in connection with cardiac echocardiography.

U.S. Pat. No. 3,881,466 discloses ultrasonic cross-sectional imaging wherein the system includes an array of transverse transducer elements which are sequentially pulsed. The rectified radio-frequency return ultrasonic echoes are converted into voltages proportional to the logarithms of the return echo amplitudes.

U.S. Pat. Nos. 3,156,110 and 3,292,018 acknowledge the weakness of bistable displays in respect of maximum possible diagnostic value in ultrasonic inspections both of living organisms and industrial flaw detection applications. These patents suggest approaches which involve the use of several ultrasonic frequencies which in turn provide return echoes differentiated by frequency to produce multicolored display patterns. Emphasis is placed upon the time-motion (TM) mode and the time exposure color photography.

U.S. Pat. No. 3,779,234 discloses the use of a sinecosine potentiometer as a means for producing B-scans. Angular information from the sine-cosine potentiometer is derived from a rotating machine as distinguished from manual motion of an ultrasonographer's hand manipulations. U.S. Pat. No. 3,690,311 discloses the use of rate derivatives of sine-cosine potentiometer angular resolvers in controlling the repetition rate of an ultrasonic pulse-echo system. Pulse repetition rate and line display are modulated so that more pulses occur during rapid hand motion than during slow hand motions.

U.S. Pat. No. 3,918,297 discloses grey-level ultrasonic imaging which requires immersion of the subject in a tank of water or other suitable conductive fluid. Pulses reflected from the specimen are passed through an acoustic focusing lens, a converter, a signal processer, and are ultimately displayed on a cathode-ray tube or light-emitting diode display device. The converter requires the use of a two-dimensional array of acoustical transducers. The reflected acoustical waves are converted into electrical signals and ultimately into binary data which is amplitude modulated in converse or complementary relationship in respect to the acoustical pulses. In three-dimensional presentations, two cathode-ray tubes are employed.

The use of logic circuitry in processing ultrasonic signals for visual display is shown in a number of patents. See, for example, U.S. Pat. Nos. 3,830,223; 3,548,641; 3,818,898; 3,856,985 and 3,885,224.

There remains, therefore, a present need for a reliable, economically practical system for taking the output of a conventional ultrasonic testing piece of apparatus and processing the signal in such fashion as to provide a grey-level visualization of the patient of specimen-generated data on a conventional storage oscilloscope.

SUMMARY OF THE INVENTION

The present invention has solved the above-described problems by providing an inexpensive, effective means of converting the output of the conventional ultrasonic test apparatus unit (either of the through transmission type or the reflected transmission type, such as a B-scan, for example) into a signal which may be visualized on a conventional storage oscilloscope in a grey-level mode or otherwise recorded or displayed.

In one embodiment, the reflected acoustical waves are converted into electrical signals which are passed through amplifying means and subsequently through linear receiver means for emitting a positive voltage signal proportional to the amplified signal. Gating means control the operating times of the linear receiver, and means are provided for modulating the output signal of the linear receiver means. Staircase generator means are associated with the modulating means to produce voltage steps proportional to the logarithm of the receiver voltage output. Dot-packing module means receive signals from the staircase generator means. Tone-burst generator means control pulse-train spacing within the dot-packing module, and storage oscilloscope means receive and visually display signals processed by the dot-packing module to provide grey-level imaging.

In the method of the present invention a specimen-reflected ultrasonic wave is converted into a related electrical function signal which is amplified and converted to a positive voltage signal related to the amplified signal. The positive voltage signal is then modulated and converted to multiple level staircase signals which are displayed in a grey-level mode on a storage oscilloscope.

It is an object of the present invention to provide ultrasonic related electrical signal processing means which permit immediate visual display thereof in a grey-level mode on a storage oscilloscope.

It is a further object of the present invention to permit economical modification of existing ultrasonic test equipment so as to convert bistable imaging into grey-level imaging which provides for more clear illustrative of the specific portion of the subject or specimen being examined.

It is yet another object of the present invention to provide such improved grey-level imaging in such fashion that existing equipment may readily and economically be "retrofit" with the improved processing equipment.

It is another object of the present invention to provide means whereby variations in speed of manual movement of an ultrasonic transducer over a test specimen may be compensated for so as to present a uniform grey-level display on a storage oscilloscope.

These and other objects of this invention will be more fully understood from the following description of the invention on reference to the illustrations appended hereto.

BRIEF DESCRIPTION OF THE DRAWINGS

FIG. 12 is a representation of a plot of the gate voltage versus time.

FIG. 13 is a plot of tone-burst voltage versus time.

FIG. 14 is a plot of the pulse voltage versus time.

FIG. 15 is a plot showing the dot-dash width buildup versus time.

FIG. 16 is a schematic illustration of a form of signal processing means of the present invention.

FIG. 17 is a plot of the staircase function generator output voltage versus the logarithm of receiver output voltage.

FIGS. 18a, 19a and 20a illustrate voltage-time plots showing examples of distinct grey levels.

FIGS. 18b, 19b and 20b illustrate several examples of transducer sweep velocity plotted against time.

FIG. 22a illustrates a form of RF booster amplifier adapted for use with the present invention.

FIG. 22b illustrates a voltage versus time plot of a typical input signal into the amplifier of FIG. 22a.

FIG. 22c illustrates a circuit diagram of a form of display sensitivity matching means.

FIG. 23a illustrates a form of linear receiver circuitry suitable for use in the present invention, and FIGS. 23b through 23e illustrate related voltage versus time plots.

FIG. 24a illustrates a circuit diagram of a form of master gate timer of the present invention, and FIGS. 24b through 24e illustrate related voltage versus time plots.

FIG. 25a illustrates a circuit diagram of a form of logarithmic tomographic function generator which produces a staircase output useful in the present invention, and FIGS. 25b through 25d illustrate related voltage versus time plots.

FIG. 26a illustrates a circuit diagram of a staircase test generator useful for confirming proper operation of the grey-level system, and FIGS. 26b through 26e illustrate related voltage versus time plots.

FIG. 27 illustrates schematically a form of grey-level visualization on a storage oscilloscope screen.

FIG. 28a illustrates a form of phase-synchronous tone-burst generator adapted for use in the present invention, and FIGS. 28b through 28e illustrate related voltage versus time plots.

FIG. 29a illustrates schematically a circuit diagram of a dot-packing module suitable for use in the present invention, and FIGS. 29b through 29f illustrate related voltage versus time plots.

FIG. 31a illustrates schematically a form of circuit diagram of a gate marker module adapted for use in the present invention, and FIGS. 31b through 31h illustrate related voltage versus time plots.

FIGS. 34 and 34a through 34d illustrate schematically an electrical circuit diagram for a form of dynamic time control gain module adapted for use in the present invention along with related signal representations.

DESCRIPTION OF THE PREFERRED EMBODIMENTS

As used herein, the expressions "test specimen" or "specimen" will refer to various types of specimens to be tested by ultrasonic means, including, but not limited to, medical tests wherein portions of a human or animal body are tested ultrasonically and specifically including, but not limited to, reflected transmission procedures, such as B-scan, A-scan, time-mode scan and through-transmission procedures. While for purposes of clarity of description, specific reference will be made to use in medical environments, it will be appreciated that other forms of test specimens may be subjected to testing by the apparatus of this invention in addition to the preferred medical use, and such other use is expressly contemplated.

Figure 1:
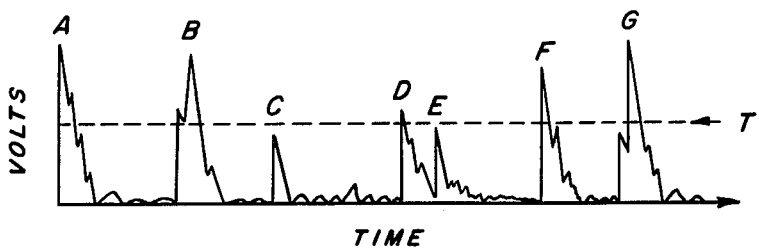
FIG. 1 is a plot of voltage versus time showing a series of reflected ultrasonic waves converted into an electrical signal.

For simplicity of description herein, frequently, specific reference will be made to reflected transmission systems. During the ultrasonic examination process, acoustical reflections occur at different times and at different amplitudes. The time between the main pulse-emission by the transducer and receipt of the reflected waves corresponds to the depth of the point of reflection within the test specimen. The amplitude of the reflected wave corresponds to the magnitude of the reflection-coefficient at the site of reflection. It is conventional to convert the reflected accoustical signal into an electrical voltage for purposes of signal processing and visual comparison. Such voltages may be monitored by direct means, such as a direct wire connection to an oscilloscope at the point designated the "video signal output" from an electronic module called the "pulser-receiver". In this fashion the time and strength of acoustical reflections may be monitored, and such a visual representation is shown in FIG. 1. Pulse A represents the electrical equivalent of the acoustical pulse going out from the transducer into the specimen. This is frequently designated as the "main-bang". Proceeding along the time reference axis, it is seen that several echoes bearing the designations B, C, D, E, F and G are illustrated. Also, a line designated T represents a possible decision threshold for use in bistable presentations. The significance of this line will be discussed in greater detail hereinafter. While in the schematic illustration of FIG. 1, the reflected waves B-G have been shown and have been provided with relatively simple shape, it will be appreciated that this simplicity has been provided for clarity of illustration. In reality, hundreds of sonic reflections sites may be present, and overlap may occur among the reflected waves. Such complexity of reflected waves can, with the equipment of the present invention, be employed to provide increased information in respect of the "fine structure" being examined.

Figure 2:
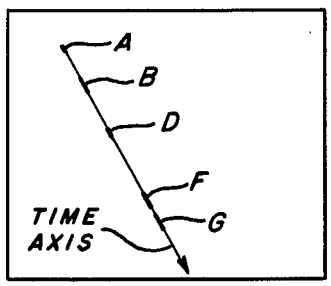
FIG. 2 is a schematic illustration of a display screen of a storage oscilloscope.

In conventional bistable ultrasound medicine, reflections which, in FIG. 1, fall below decision threshold T would not be pictorially recorded. While the decision threshold T, for simplicity of illustration, has been shown as involving a straight line parallel to the time axis, it will be appreciated that sometimes these decision thresholds become more complicated, such as those involving time-derivative functions of the reflection signal, for example. An essential principle of bistable display is to fail to pictorialize any reflection which fails to exceed the decision threshold T. In FIG. 1, for example, reflections, B, D, F and G would be recorded and pictorially displayed, whereas reflections C, E would not. As is shown in FIG. 2, which represents schematically the displayed screen of a storage oscilloscope, in a bistable system the outgoing pulse or main-bang A would be shown as would the reflection signals B, D, F and G which have exceeded decision threshold T. The time axis is illustrated as being oriented angularly downwardly and to the right with a downward direction indicating increased time.

Figure 3:
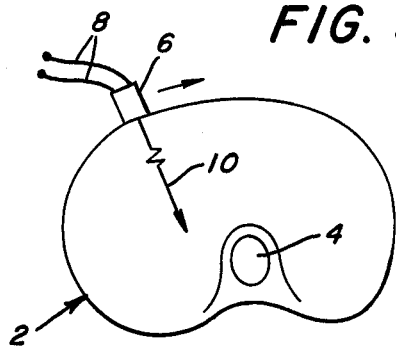
FIG. 3 is a schematic illustration of an ultrasonic probe positioned against a human specimen.

Referring to FIG. 3, the general concept of data-gathering described above will be illustrated. As is shown in FIG. 3, there is a specimen 2, which, in the form shown, is a cross-section of a human patient's abdomen, the spinal column is represented by the reference number 4. A transducer 6 with appropriate acoustical coupling medium interposed is in contact with the specimen 2. Electrical wires 8 energize the transducer 6 and serve to return an electrical signal corresponding to the reflected acoustical waves. An acoustical pulse entering the patient is indicated generally by the number 10. As the physician slides the transducer 6 over the lubricated exterior surface of the specimen 2 in the direction generally indicated by the arrow in FIG. 3, corresponding time axis lines (such as the one shown in FIG. 2) are swept on the face of the storage oscilloscope. On the storage oscilloscope, once the time axis line passes a given region, those regions indicated by the dark bars in FIG. 2 remain electronically illuminated.

Figure 4:
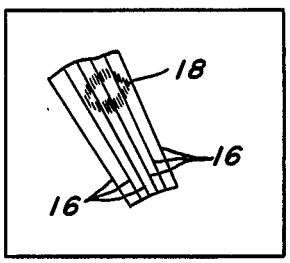
FIG. 4 is a schematic illustration of a storage oscilloscope showing a visual display generated by a number of pulses within a single transducer sweep.

Subsequent and repetitious pulses during a pass of the transducer 6 over the surface of the specimen 2 will result in generation of additional time axis lines with bars and dots. The time axis lines remain generally parallel and advance sequentially in a particular direction on the storage oscilloscope as is shown in FIG. 4. A plurality of time axis lines 16, are shown with the first such line generated appearing toward the left of the screen, and those generated sequentially thereafter being shown to the right thereof. The image 18 created by the series of time axis lines 16 is the result of the cumulative effect of representations such as that shown for the individual line in FIG. 2.

Figure 5:
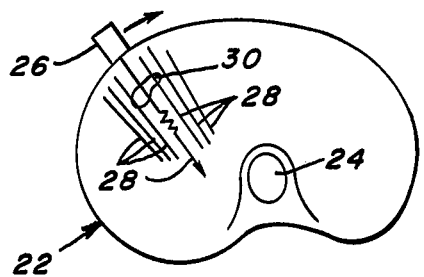
FIG. 5 is a schematic section of a human specimen similar to that of FIG. 3 showing a simulated plurality of ultrasonic pulses along a manual sweep in relationship to an organ of the body.

As is shown in FIG. 5, the specimen 22 has a spinal column 24 and a transducer 26 has been subjected to repeated pulsing during a single pass in the direction of transducer movement indicated by the arrow. This results in generation of a number of pulses 28 from a transducer 26 into the specimen 22 which in turn generate reflected pulses (not shown in this view) along the time axis lines to generate the image 18 of the gall bladder 30 of specimen 22.

As has been mentioned above, the currently available, high resolution storage display oscilloscopes do not store images in intermediate shades of grey. These oscilloscopes once subjected to electrical amplitude and coordinate information will either print white (actually generally greenish) spots or nothing at all (black). Also, the likelihood that such storage oscilloscopes actually "capture" a point that sticks in the stored modes is dependent in part upon the speed of the sweeping motion of the time-axis line. More slowly swept lines tend to stick better than rapidly swept lines.

Figure 6:
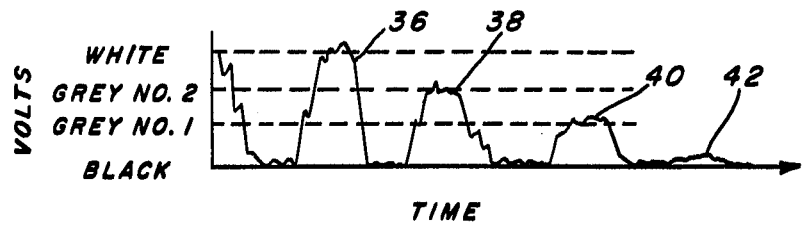
FIG. 6 shows a voltage versus time plot representing reflected ultrasonic waves.
Figure 7:
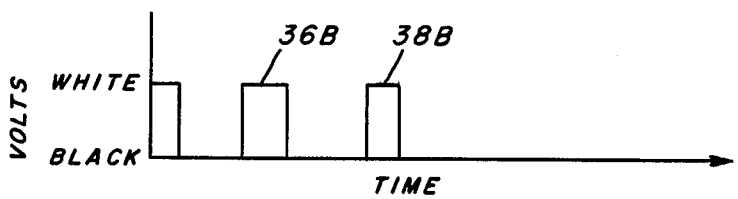
FIG. 7 represents a bistable illustration of the voltage-time plot of FIG. 6.
Figure 8:
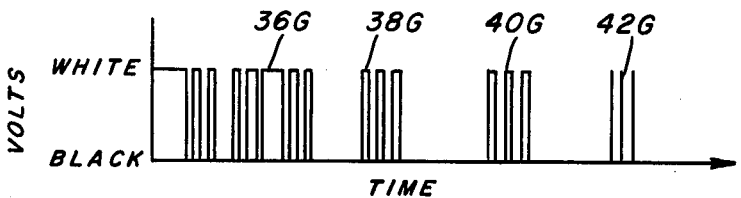
FIG. 8 represents a grey-level presentation of the voltage-time plot of FIG. 6.

Referring now to FIGS. 6 through 8, a direct comparison between the visual output of a bistable presentation as distinguished from a grey-level presentation will not be provided. As is shown in FIG. 6, waves 36, 38, 40 42 have different voltage amplitudes. On the voltage scale in FIG. 6 there are indicated voltage levels corresponding to black, grey #1, grey #2 and white. Assuming that in the bistable display, a decision level (not shown) were placed halfway between grey #1 and grey #2, FIG. 7 shows the display which would appear. As only waves 36 and 38 (of the numbered group) extend beyond such a decision level, in FIG. 7, the bistable presentation shows corresponding square waves 36B and 38B. There is no representation of waves 40, 42 of FIG. 6. Also lost in the bistable display is information regarding the relative strength of waves 36 and 38.

Figure 9:
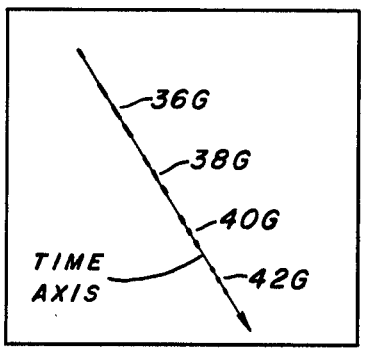
FIG. 9 represents a schematic illustration of a presentation on a storage oscilloscope screen.

Referring now to FIG. 8, there is shown a greylevel presentation corresponding to the waves of FIG. 6. Not only are all of the waves represented in FIG. 8, by the designations 36G, 38G, 40G, 42G, but also there is an indication as to the relative strength or voltage amplitudes of the waves. The higher the voltage level of wave 36, 38, 40, 42 of FIG. 6, the wider the corresponding presentation on FIG. 8 in waves 36G, 38G, 40G, 42G. Thus, the widest waves 36G correspond to wave 36 of FIG. 6, and the narrowest waves 42G correspond with wave 42 of FIG. 6. The presentation of the grey-level image on the storage oscilloscope corresponding to FIG. 8 is shown in FIG. 9. As is noted along the time axis reference, the presentation of 36G is represented by relatively long bars. The 38G reference are shorter bars than 36G, while the 40G bar is shorter than 38G. The waves 42G are represented by a series of three dots corresponding to the three lines shown for 42G in FIG. 8. It will be appreciated, therefore, that each reflection registers as either a dot or a bar and the relative amount of illuminated "fill-in" between adjacent dots or bars increases for higher reflection amplitudes.

Figure 10:
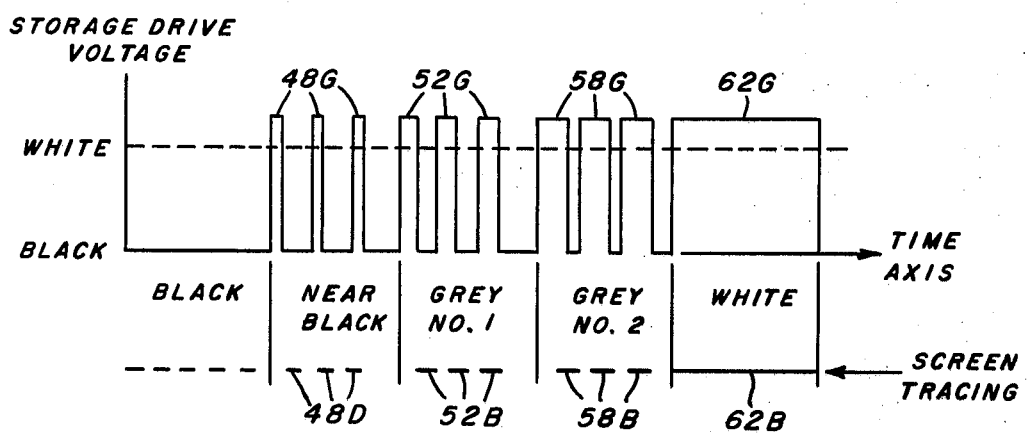
FIG. 10 illustrates a schematic representation of a grey-level voltage-time plot.

The correspondence between the plot of time axis versus storage drive voltage on the one hand, and the presentation on the storage oscilloscope screen on the other, is shown schematically on FIG. 10. As is shown in the zone labeled black, the voltage has zero amplitude, and there is merely the dot matrix lightly shown in terms of the corresponding screen tracing. In the zone labeled "near black", there are shown three relatively narrow square-like storage drive voltages labeled 48G. The corresponding oscilloscope presentation consists of three dots labeled 48D. In the next zone along the time axis, there is shown a group of three square-like storage drive voltages labeled 52G which are of a greater width than the square waves 48G. The corresponding oscilloscope screen tracing display consists of three bars labeled 52B. Considering next grey-level #2, there are shown three square waves 58G which are wider than square waves 52G. The corresponding oscilloscope tracing display are three bars 58B which are longer than bars 52B. Finally, in the zone designated white, the square-like storage drive voltage waves occupy the full zone, which has been labeled 62G, and has a corresponding screen tracing 62B which runs across the complete white zone. It will be appreciated that the transition from the narrowest dot 48D shown to the widest bars or dashes 62B may be accomplished in stepwise or continuous fashion. For example, I have found that a six-step grey-level imaging system (employing black and white extremes as two steps) provides an effective range in terms of grey-level display of varying amplitudes for use on a storage oscilloscope, such as that marketed under the tradement "Tektronix Type 611", for example.

Figure 11:
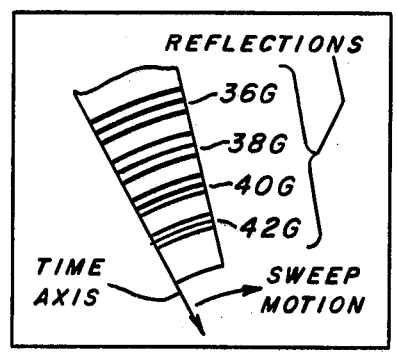
FIG. 11 represents a developed visualized picture of a plurality of ultrasonic pulses within a sweep as shown on a storage oscilloscope screen.

Referring now to FIG. 11, there is shown an illustration of the result of a number of pulsings during one sweep of the transducer by the physician across a patient or by other tester across any test specimen. By comparison with FIG. 9, it will be seen that what has occurred is that each successive pulse has resulted in enlargement of the zones shown in FIG. 9 in the general direction shown by the arrow labeled SWEEP MOTION. In effect, the dots and bars or dashes blend into bands of variable widths wherein the widths are indicative of the reflection amplitude. For purposes of simplicity of illustration, the bands for each discrete grey-level step shown in FIG. 11 are generally uniform in width. As a result of the velocity-correction circuitry disclosed hereinafter, such uniformity in width is insured even under greatly varying manual sweep velocities.

As is shown in FIG. 12, square waves which are gate pulse waves 70 are formed whenever the time axis line is present, e.g. during the first 300 microseconds, for example, after the "main-bang" pulse, which is the period when most reflections containing pictorial information are received. The duration of the time axis line is proportional to the maximum depth of view within the patient or specimen. As is shown in FIG. 13, whenever the gate pulse 70 is on, a tone burst 72 is generated. It is noted that the tone burst 72 starts in a positive going direction. The tone burst will also have the same number of cycles from burst to burst which may be about 300 cycles per single gate pulse, for example. The tone burst (which may range in frequency from about 500 to 1,000 KHz, for example) serves to determine the spacings between grey-level dots or bars and also establishes the horizontal band continuity shown in FIG. 11.

Referring now to FIG. 14, there is shown a series of spike-like electronic pulses 74 which are generated as a consequence of differentiating the positive-going slopes of each cycle of tone burst 72. As is shown in FIG. 15, the spike-like (short) electronic pulses 74 of FIG. 14 become elongated into bar-shaped pulses 76. The extent of elongation depends upon the function of the amplitude of the reflection signals thereof (such as the logarithm) occuring during the gate pulse 70 "on" time, and such reflection signals orignate from within the patient. It will, therefore, be appreciated that a significant aspect of grey-level imaging on bistable storage oscilloscopes is the modulation of the width of the dot or bar pulses by patient-originating data, and it is such modulation that contributes to the new dimension of greyness which is displayd upon the storage oscilloscope.

Referring now to FIG. 16, there is shown an ultrasonoscope 90 which may be any conventional variety. A suitable instrument is the Picker Echoview VI vertical plug-in. The ultrasonoscope 90 has a transducer 92 which is adapted to be acoustically coupled to the test specimen. An RF monitor 94 is added to the ultrasonoscope 90 at vertical plug-in 96 of the ultrasonoscope 90. In operation, the transducer 92 will be energized to emit an ultrasonic wave into the specimen and, in turn, will receive reflected waves. The reflected waves are converted to electrical voltage signals which emerge from the ultrasonoscope 90 through RF monitor 94. The monitored signal is amplified by RF booster amplifier 100 which, in the form shown, contains both a continuous or Vernier gain control 102 and a step-wise gain control 104. The amplified signal by way of lead 106 is introduced into linear receiver 112. At the lower left-hand portion of FIG. 16 there is shown the gate pulse portion 90A of ultrasonoscope 90 which emits an external gate pulse on lead 114 which is received by master or gate timer 116. Master gate timer 116 emits a gate signal 118 which is introduced into linear receiver 112. Linear receiver 112 is activated by gate signal 118 and, in turn, emits output positive-going only voltage signal on lead 120. The voltage signal on lead 120 is directly proportional to the peak-to-peak amplitude of signal on lead 106. It will be appreciated that the gate signal 118 determines the active or on-time of the linear receiver 112 and, as a result, the on-time of the entire grey-level system. The master or gate timer 116 establishes the length of the gate pulse, such as was shown in FIG. 12. This gate pulse is initiated at the exact time that the external gate pulse signal on lead 114 from the ultrasonoscope gate portion 90A begins its "on" condition. The gate portion 90A typically remains on for a predetermined period of time after the outgoing wave is generated by transducer 92.

In the form illustrated, the receiver output signal on lead 120 is converted by tomographic function generator 128 into a nonlinear signal, preferably monotonic. In the form shown, the tomographic output on lead 130 becomes, to the first approximation, the stepwise quantization (staircase) of the logarithm of the receiver output signal on lead 120. In the form of system illustrated, an assembly of slide potentiometers 132 is operatively associated with the tomographic function generator 128 in order to allow the examining physician or ultrasonographer some degree of freedom in selecting the dynamic characteristics of the tomographic output signal on lead 130. The effect of moving the slide potentiometer position is to change the overall contrast characteristics (similar to photographic "gamma") of the grey-level imaging system. This contrast variability is of importance when the ultrasonographer attempts to diagnose certain pathologies, such as cystic regions, abscesses and blood clot plaques along the aorta, for example.

In the form of tomographic function generator 128 illustrated, it is contemplated that the tomographic function generator 128 will have six possible states, each of which corresponds to one of six permissible levels to be visualized through the grey-level system. In general, it is preferred that about four to ten output grey levels be employed.

A specific example of how this portion of this system functions will now be considered. For linear receiver output signal on lead 120 ranging from 0.05, 0.5, 5.0 volts DC, the tomographic function generator 128 may produce outputs of 0.8, 2.4, 4.8 volts DC in the output signal on lead 130, respectively, for typical slide potentiometer settings. The only possible outputs of tomographic function generator 128 in this example would occur along six possible specific steps of 0.0, 0.8, 1.6, 2.4, 3.2, and 4.0 volts DC, for input voltages 120 ranging continously from 0.02 to 4 volts, peak to peak.

It has been found that six steps produced by tomographic function generator 128 represent a suitable number of shades which may be easily displayed on storage oscilloscope 138. A suitable form of storage oscilloscope for use in this invention is the one sold under the trademark Tektronix 611 Storage Oscilloscope.

The tomographic function generator output signal on lead 130 is fed through staircase generator 140, which in the form shown is equipped with a through or test switch 142. Whenever the switch is in the "test" position, the gating signal on lead 144 initiates a ladder-like voltage test wave form 148 (FIG. 17). This voltage test wave form 148 serves to check out the performance of the grey-level imaging system. It will be noted, that the six steps correspond in voltage levels to the voltage expressed in the example set forth above. The marker pulse 149 provides a convenient reference to gauge the displayed width of the first grey-step (which is black). Once the test has been satisfactorily completed, the switch 142 is changed to the "through" position, and specimen-originated signals are permitted to pass from the staircase generator 140 to dot-packing module 152 by lead 150.

Whenever linear receiver 112 is activated by gate signals 118, the modulating input signal on lead 150 (which signal represents six-level staircase signals corresponding to specimen-generated data) is introduced into dot-packing module 152. The gate signal 118 activates phase-synchronous tone-burst generator 160 whose output signal on lead 162 enters dot-packing module 152 and establishes the pulse-train spacing within the dot-packing module 152. The width of the dots or bars in the signal on lead 164, which emerges from dot-packing module 152, are stepwise variable for any of the six discrete choices as governed by the specimen-originating signals on lead 120.

The video switch control module 166 permits operation of the grey-level system, reversion back to bistable performance or remote automatic alternation between the grey-level and bistable presentation by means of push-button switch 168. Switch 170 provides positioning at the video control switch module 166 at grey-level performance, bistable performance or automatic alternation between grey-level and bistable performance. Push-button switch 168 permits remote control selection from among the three positions. In the event that switch 166 is placed in the bistable position, ultrasonoscope 90 emits a bistable signal on lead 174 into video switch 166. Regardless of which type of signal is to be displayed, the pictorial information is provided on the signal on lead 176 to the Z-input (or write gun) of the storage oscilloscope 138.

The dot-packing module 152 is driven by sinusoidal reference waveforms 162 from phase-synchronous tone-burst generator 160, which, in turn, acts responsive to the receiver gate signal 118. The dot-packing module 152 also acts responsive to receipt of stepwise variable patient information by signals on lead 150. The dot-packing module 152 responsive to receipt of signals on leads 150, 162, produces a substantially square output pulse on lead 164 whose on-time duty factor is discretely variable at zero %, 20%, 40%, 60%, 80% and 100%, respectively, as commanded by signals on lead 150 in the form selected for illustration. The Z-axis threshold of storage oscilloscope 138 is internally adjusted to store signals on the scope screen whenever the Z-input signal on lead 176 exceeds a predetermined voltage level, which is preferably slightly below the peak of the output pulse on lead 164.

In a preferred form of the present invention, means are provided for effecting substantially the same amount of "blending" between the dots and bars or dashes so that as displayed on the screen of the storage oscilloscope 138, there is compensation for variations in speed of the physical movement of the transducer 92 along the path of sweep. The result is that the blending between successively generated time axes will be effected smoothly, regardless of whether the sweep of the transducer 92 was effected in a fast or slow or intermediate speed mode. FIGS. 18a, 19a and 20a illustrate different storage oscilloscope display screen images corresponding to the related plots of sweep velocity versus time shown in FIGS. 18b, 19b, 20b, respectively. Referring now to FIGS. 18a, 19a and 20a, there is shown a reference time axis line 180 which is illustrative of movement of transducer 92 on a single manual sweep at uniform speed. As is shown in FIG. 18b, the velocity between times $T_1$ and $T_2$ has remained constant. Generated line 182 is, therefore, parallel to reference line 180. As is shown in FIGS. 19a and 19b, where the sweep velocity is greater at $T_1$ than at $T_2$, generated reference line 184 diverges generally upwardly with respect to reference line 180. Finally, in connection with FIGS.

20a and 20b wherein the sweep velocity is lower at $T_1$ than at $T_2$, the generated reference line 186 converges generally upwardly with respect to reference line 180.

As is noted in FIGS. 18b, 19b and 20b, depending upon the sweep motion, which is generally upwardly linear or arcuate across the specimen, a sweep velocity may become a step function or a trapezoidal function, for example. The manner in which the functions shown in FIGS. 18b, 19b and 20b are generated as analog electrical functions will be described below. When such analog electrical functions are applied directly to modulate the intensity of the "write electron-gun" portion of oscilloscope 138, then proper blending action is received along those linear and arcual sweeps.

Considering now more specifically, the blending action being maintained in a substantially uniform form by compensating for sweep speed variations, reference is made once again to FIG. 16.

The interface circuitry 194 of the ultrasonoscope 90 emits an X-deflection signal 196 and a Y-deflection signal 198. The combination of signals 196, 198 provides for proper display and orientation of the time axis line on the oscilloscope 138. For example, when waveforms 196, 198 are about equal in magnitude, a 45° diagonal time axis line is displayed. However, when the amplitude of signal 198 exceeds the amplitude of signal 192, the time axis line becomes nearly vertical. The relative amplitudes of waves 196, 198 as well as their DC (position) offset position voltages all occur in response to the physician's or ultrasonographer's manipulation of the transducer 92 along the patient or other specimen.

Coordinate catchers 200, 202, sample the analog electrical voltages that correspond to the beginning, end of the X-deflection signal 196 and the beginning, end of the Y-deflection signal 198, respectively.

In order to perform these functions, the coordinate catchers 200, 202 must be provided with an indication of when to become activated. An example of how this may be accomplished will now be considered. The gate signal 118 from gate timer 116 is introduced into the gate marker module 204. Gate marker module 204 provides a short trigger pulse 206 corresponding to the starting edge of gate pulse 118 and also a short trigger pulse 208 which corresponds to the stopping edge of gate pulse 118. In this manner, both the upper and lower limits of the time axis are always defined in time and by applying such pulses 206, 208 to coordinate catchers 200, 202, four analog voltages are derived which tell how both the top (starting) and bottom (stopping) ends of the time axis move during the scanning action of transducer 92 across the specimen. Pulses 206, 208 are positive going. The output signals 220, 222, 224, 226 have the same magnitude as the signals 196, 198 have, respectively, and the distance between 220 and 222, as well as the distance between signals 224 and 226 correspond to the peak-to-peak amplitudes of waveforms 196, 198, respectively.

When the beginning coordinate signals 220, 224 are fed to coordinate velocity calculator 228, an output voltage 230 that represents the start velocity is obtained. The voltage 230 corresponds approximately to the vector sum of horizontal and vertical start velocities (at the beginning of the time axis), and voltage 230 can be stepwise scaled in response to velocity gain adjustments 229, 233. Similarly, coordinate signals 222, 226 are fed to coordinate velocity calculator 232, and output voltage 234 represents the total stop velocity. Both voltages 230, 234 are applied in concert with gate pulse 118 to dynamic time-controlled gain (TCG) module 240, to produce waveform 242 that represents the negative (upside down) version of FIGS. 18b, 19b, 20b. Waveform 242 feeds into special wired interface circuitry 244 of storage oscilloscope 138. The specially wired circuitry 244 serves to increase write-gun brightness in proportion to sweep velocity everywhere along the time axis line.

As is shown in the lower right-hand corner of FIG. 16, the regulated power supply 250 may conveniently consist of a connection to an AC line, which, through suitable switches, permits delivery of either plus 20 volts DC or minus 20 volts DC to all units to be energized within the system.

Figure 21:
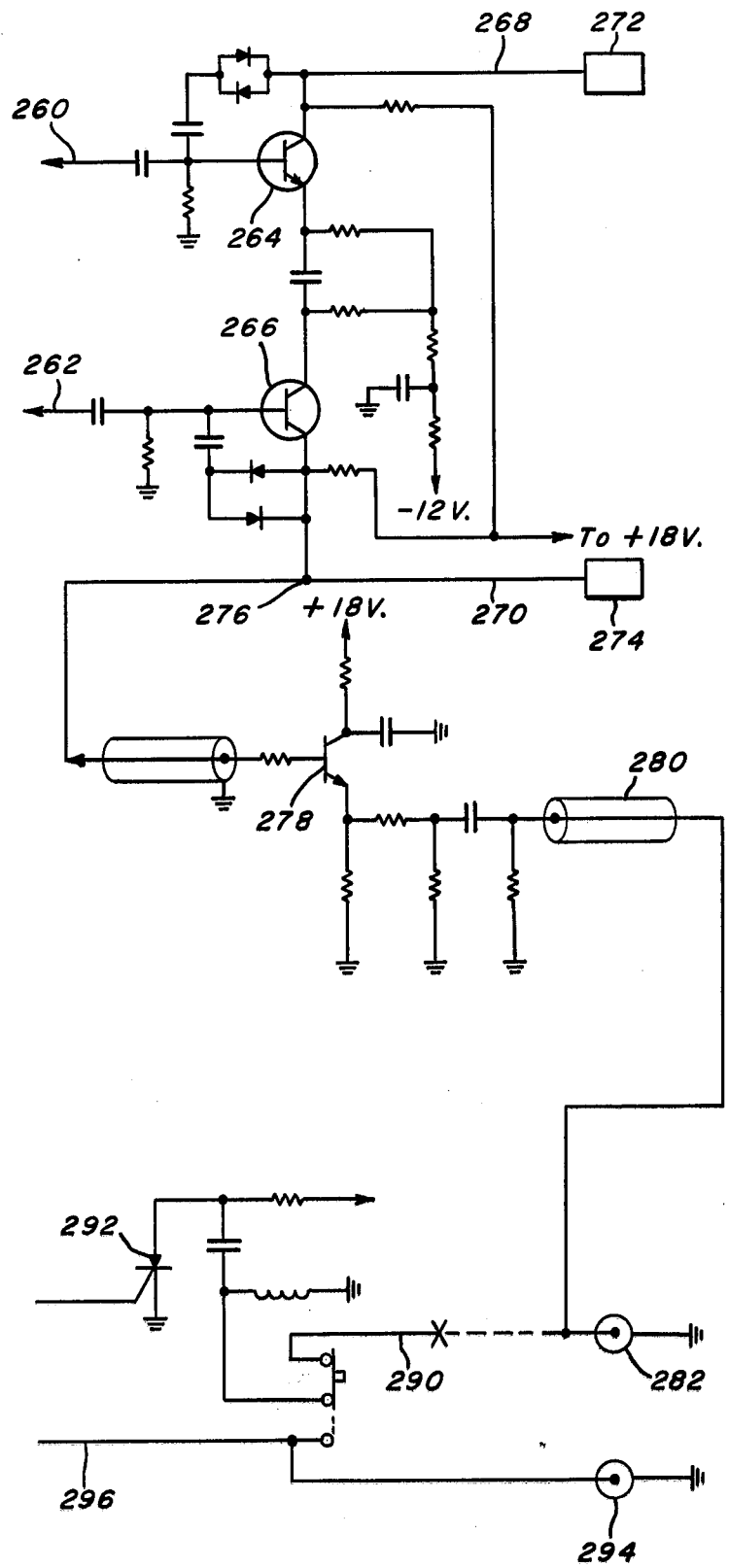
FIG. 21 illustrates portions of the electrical circuitry of an ultrasound instrument which may be employed with the present invention.

Referring now to FIG. 21, there is shown a suitable, vertical, plug-in circuit arrangement for use in creating the RF monitor 94 connection with the ultrasonoscope 90. The ultrasonoscope may conveniently consist of a unit such as that marketed under the trademark Picker Echoview VI vertical plug-in, modified in accordance with the circuitry shown in portions of FIG. 21 shown located below junction 276 and described herein.

The vertical plug-in module portion of the ultrasonoscope in the form shown in FIG. 21, takes care of processing the return echo signals at the receiver circuit board. Conventional means (not shown) may be employed to amplify the RF echo signal from the transducer 92. The amplified RF echo return signal is applied at junction 260, 262. The signal is then passed through the intermediate electrical components into two differential limiting amplifier transistors 264, 266, and the output along lines 268, 270 is connected via pin connectors 272, 274 to the video circuit board on the main frame of the storage oscilloscope. The modified circuit portion begins at junction 276. The RF signal at junction 276 is fed into the emitter-follower transistor 278, which acts as a line driver to drive about six feet of external, coaxial line 280 connected to the grey-level system. Wire 290 is normally connected to jack 282, but this connection is broken, and the system no longer works in the through-transmission mode. The SCR pulser 292 drives transducer connection 294 only in the reflection mode, i.e. the same transducer both sends and receives the acoustical wave, and the RF monitor signal from the receiver is made available at junction 296.

While most of the components illustrated and employed in the specific example given in FIG. 16 will be well known to those skilled in the art and need not be discussed in detail herein, examples of suitable components will be provided in the interest of presenting a full and complete disclosure.

Referring now to FIG. 22a, a suitable type of radio frequency booster amplifier 100 will now be considered in detail. Radio frequency voltage signals from the vertical plug-in of the ultrasonoscope 90, which have been indicated as the signals on lead 94 in FIG. 16, are fed into the RF booster amplifier at RF input terminal 302. These signals are typically sinusoidal such as is indicated by wave 304 in FIG. 22b, and are positive and negative going with maximum peak-to-peak amplitudes approaching 0.8 volts peak-to-peak, for example. As shown in FIG. 22a, +V is, in the example given, 20 volts DC, and −V is minus 20 volts DC. Transistors 306, 310 work in concert to amplify voltages 304 tenfold (20 dB gain) when monitored across the primary winding 308 of RF transformer 312. Transformer 312 preferably has a 1:1 turn ratio. Transistors 306, 310 work as a single-ended driven differential stage, and such differential design is employed because capacitors are avoided. The avoidance of capacitors eliminates the "recovery-time problem", i.e. some amplifiers become inactive for the first few microseconds following the initial transducer-generated outgoing ultrasonic wave or main-bang signal.

The elimination of the recovery-time problem is particularly important when visualization of superficial features at shallow depths within the patient or specimen is desired by the examining physician or ultrasonographer. Secondary winding 320 of transformer 312 drives emitter-follower transistor stage 322 which has sufficient drive capability at RF output terminal 324 to feed into coaxial line capacitance and posterior circuit loading without allowing the output signal at 324 to suffer deleterious effects such as distortion and attenuation.

Gain adjustment is important because frequently the ultrasonographer desires to switch manually between the ordinary bistable display and the grey-level display by use of video switch 166. During such switching, both the bistable and grey-level mode must have matched display sensitivities. Such matching may be accomplished by a 6 dB/step-gain switch 326 and a Vernier gain potentiometer 328 which finally adjusts gain within each 6 dB step. The output voltages available at RF output 324 may range from about 1.0 volts peak-to-peak to about 10 volts peak-to-peak, and are typically about 2.5 volts peak-to-peak, for example. The ratio of output to input voltages may range from about 3:1 to about 50:1 with about 10:1 being typical, although some variability is desirable when the ordinary (2.25 MHz) transducer is removed, and specialized transducers are employed (such as 5.0 MHz transducer, for example).

FIGS. 23a through 23e illustrate a suitable form of linear receiver 112 which may advantageously be employed in the present invention. The RF signal from RF booster amplifier 100 is fed into the linear receiver at 350. (Transistors 352, 354 work in concert as a single-ended driven differential stage to produce about 15 volts peak-to-peak, for example, in primary winding 356 of RF transformer 358, which preferably has a 1:1 turn ratio.) The differential design and transformer coupling method are employed for the same purpose as was discussed above in connection with the detailed description of an example of an RF booster amplifier. Secondary winding 360 of transformer 358 drives bases of transistors 364, 366, whose emitters act as full wave rectifiers producing waveforms 368, 370, 372 shown in FIG. 23c from echo signals 374, 376, 378, respectively, as shown in FIG. 23b. Filter 380 acts as a two-stage pi-network low-pass filter that optimally reduces ripple in waves 368, 370, 372, while simultaneously preserving the temporal shortness in waves 368, 370, 372, such as is shown in waves 382, 384, 386 in FIG. 23d.

The grey-level system is active only during the forward swept time (approximately 300 microseconds) of the time axis line on the oscilloscope display. As waveforms 378, 372, 386, for instance, happen to occur after 300 microseconds beyond the main-bang pulse, waveform 386 must not be displayed. Otherwise, waveform 386 would appear in some meaningless location on the storage oscilloscope screen, such as, for example, along a "retrace" line. Quenching action of waveform 386 is accomplished by accepting the gate signal 388 (FIG. 23e) at gate end location 390, and by using transistors 394, 396 to "short circuit" unwanted signals from the output emitter-follower transistor 392. In order to prevent transistor 392 from burning out during short-circuiting action, resistor 398 is employed to act as a buffering component. Transistor 400 is the line driver that feeds the video output at 402 to the tomographic function generator 128 part of the grey-level system.

Referring now to FIG. 24a, there is shown a form of master gate timer 116 (FIG. 16) which is suitable for use in the present invention. External gate signals from the rear of the ultrasonoscope 90A enter at input contact 420. The signals entering at 420 are differentiated by resistor 422 and capacitor 424 to activate one-shot multivibrator indicated generally as 426. The signal 428 entering at 420 is shown in FIG. 24b, and the signals which have passed through resistor 422 and capacitor 424 are indicated as 430, 432 in FIG. 24c. The negative-going pulse at contact 446 of the multivibrator 426 drives the gate circuit to produce a master gate pulse 448 shown in FIG. 24d and emerging from gate output 450 after passing through circuit 449. The length of this pulse 448 is governed by capacitor 456 and resistor 458 which determine the magnitude of current from the 2N3906 transistor 460, which acts as a constant current source. The length of the pulse 448 can be adjusted in a Vernier fashion by placing resistor 462 with a tapped resistor (potentiometer or trimpot) in which the gate length time becomes proportional to the fraction of resistor 462 sampled by capacitor 456. Such Vernier adjustment may be desirable because a physician or other ultrasonographer may want to control the length of the time-axis line (and the temporal duration during which the entire grey-level system is active). Signals at junction 470 also trigger a short one-shot multivibrator 472 in order to produce pulses 474 shown in FIG. 24e. Such pulses are desirable to trigger oscilloscopes through output connection 476 for diagnostic equipment-check purposes. (See the trigger out contact in FIG. 16.)

Referring now to FIGS. 25a, 25b, 25c and 125d, a suitable form of logarithmic tomographic function generator which may be used for element 128 illustrated in FIG. 16 will now be considered. As is seen in the upper left-hand portion of FIG. 25a, a video signal is received at input 486 and drives resistor 488 and diodes 490, 492 to produce a small voltage at junction 494. The voltage is directly proportional to the logarithm of the video signal introduced at input 486. Differential amplifier employing transistors 496, 498 restores the logarithmic signal appearing at 494 to the original peak-to-peak amplitude of signal 486 measured at point 500. For purposes of this illustration, the system is deemed to be operating in the dynamic range of about 25 dB. By changing from a linear to logarithmic video signal, at 500, the most suitable integral spacing (at a ratio of about 2:1 signal changes) occur for adjacent grey-level displays. Transistor 512 drops the DC offset voltage at junction 500 down to zero volts (referred to herein as ground potential), and transistor 514 is the emitter-follower stage that drives offset potentiometers 516, 518, 520, 522 and 524. Offset potentiometers work as follows. Video voltage, in logarithmic form as is shown by wave 536 in FIG. 25b, is retarded in DC levels at 538 (FIG. 25c) in proportion to the upper positions of potentiometers 516 through 524. Such DC level retardation is caused by constant current sinks 540, 542, 544, 546, 548. Whenever the wiper voltages exceed zero volts, transistors 550, 552, 554, 556, 558 are turned on. These transistors 550–558 in turn cause level-shifting transistors 576, 578, 580, 582, 584 to also turn on, thereby engaging currents in resistors 586, 588, 590, 592, 594 and the collective currents on bus 596, represents one of the six possible discrete imaging levels in the present six-level example. These steps are set by gain trimpot 612 to cause the step hike to be about 0.8 volts, and hence each step being zero, 0.8, 1.6, 2.4, 3.2, and 4.0 volts DC in the present example. These discrete voltage levels are led into line-driver output transistor 614 to provide one of six possible grey steps at output 616. Three of these steps are summarized at 618 in FIG. 25d. The particular (logarithmic) voltage interval that causes transitions between each of the six-step output voltages, in the present example, is determined by the settings of the potentiometers 516, 518, 520, 522, 524. These settings, therefore, regulate the contrast in dynamic range of the display (six-step) grey-levels on the oscilloscope 138. Resistor 620 sets the zero volts DC level for the first or black grey-level step.

Referring now to FIGS. 26a, 26b, 26c, 26d and 26e, there is shown a form of staircase generator which is suitable for use as staircase generator 140 in FIG. 16. The operation of the staircase generator in test mode is very similar to the manner in which the tomographic function generator 128 operates. However, instead of responding to a video signal (or its logarithm), the staircase generator produces six discrete steps in response to the ramp waveform which is initiated by the gate pulse (shown in FIG. 26b) introduced at input 640. When the gate pulse at input 640 goes "on", (for example, a positive zero volts DC), transistor 642 turns on, thereby causing the voltage across the resistor 644 to drop toward zero volts. This, in turn, causes transistor 646 to turn "off", i.e. to stop conducting current. Transistor 648 acts as a continuous current source.

As a result, when transistor 646 turns on during the period when the gate input 640 is "active", transistor 648 charges capacitor 650 along a linear ramp waveform 652 shown in FIG. 26c. Emitter-follower 666 drives all decision threshold stages by 668, 670, 672, 674, 676 at junction 678. The combinations of resistors (such as resistors 680, 682 associated with stage 672) simulate the potentiometer retardation action previously discussed in connection with the tomographic function generator 128. FIG. 26d shows the retarding action of resistors, such as 680, 682, to downwardly deflect the ramp waveform below the decision thresholds. Bus 694 develops a staircase voltage 696 (see FIG. 26e) in which each step (0.0, 0.8, 1.6, 2.4, 3.2 and 4.0 volts DC, in the example given herein) occurs at approximately 40 microsecond intervals. Circuit portion 698 acts to produce an initial transient 700 (see FIG. 26e) to mark the beginning of the stepwise staircase waveform. This waveform 699 produces a line followed by grey "wedges" along the screen of oscilloscope 138. FIG. 27 illustrates the various levels as developed on the screen of oscilloscope 138. As is shown in FIG. 27, line 702 represents a grey-level #1 or black border line, and it is developed through sequential time-axis line scans, as the transducer is slowly swept in a direction moving generally from left to right. Succeeding lines moving downwardly represent successive stages of relative lightening moving from level #1 through level #6, which has a lower borderline 704.

Referring now to FIGS. 28a, 28b, 28c, 28d, 28e, there will be disclosed a form of phase-synchronous tone-burst generator suitable for use as element 160 shown in FIG. 16. The phase-synchronous tone-burst generator produces a square packet of RF energy 714 (FIG. 28c) which is generally precisely in phase with the command signal or gate pulse 716 (FIG. 28b). Although the individual frequency is continuously adjustable by means of adjustable capacitor 718, the start of the square packet of RF energy is always positive going, such as is indicated at 720 in FIG. 28c.

Transistor 728 is a current source that keeps tapped inductor 730 "charged" with energy in accordance with the formula $W = \frac{1}{2}Li^2$, wherein $W$ = energy, $L$ = inductance and $i$ = current. When gate pulse 716 is applied to gate input terminal 732, transistors 734, 736 act collectively to turn off current source transistors 728, and when this occurs, inductor 730 "free-wheels" with capacitor 718 to produce exponentially damped oscillation 738 (FIG. 28d). Field-effect transistor 752 acts as a regenerative element to form a Hartley oscillator circuit through inductive tap 754. The degree of regenerative feedback is established by decay potentiometer 756. When the degree of regenerative feedback is properly adjusted, exponentially damped oscillation 738 (FIG. 28d) squares off to a waveform, such as that indicated by 714 in FIG. 28c. However, too much regeneration could cause the waveform to have the shape of waveform 758 in FIG. 28e, which exhibits exponential growth.

Transistor 760 causes the return point 762 to have a lower DC voltage level when the circuit is quiescent (recharging) than when the circuit is active (producing a tone). Such dropping of DC voltage levels causes diode 764 to "clamp" the inductor-capacitor (730, 718) combination abruptly, thereby preventing unwanted residual oscillations between tone bursts. Clamp potentiometer 766 acts as a fine tuning device to set the minimum required clamping action needed. If too much clamping is employed, this excessive clamping interferes with the decay potentiometer 756 setting. Amplifier 778 may be a conventional radio frequency amplifier that raises the radio frequency tone burst (for purposes of this example, approximately 600 to 1,000 KHz) signal (0.4 volts peak-to-peak) sampled at junction 780 to levels of about 5.0 volts peak-to-peak compatible with the dot-packing module's requirements as made available at tone-burst output 782. Only a very small voltage, for example, in the neighborhood of 10% is sampled at junction 780, then amplified in order to prevent any possible influence of the load (the dot-packing module) upon the critically damped oscillating circuitry (730, 718, 752 and 756).

Referring now to FIGS. 29a, 29b, 29c, 29d, 29e and 29f, there is shown a form of dot-packing module which is suitable for use as dot-packing module 152 in FIG. 16. Whenever the tone-burst signal entering at tone-burst input 800 exceeds a predetermined voltage $V_1$, such as 1.0 volts DC, for example, as is shown by the wave 802 in FIG. 29b exceeding the dotted $V_1$ reference line, transistors 806, 808 develop square-waves that are differentiated by resistor 810 and capacitor 812 to produce double-spiked waves at junction 820, such as are shown in FIG. 29c and indicated by the reference number 822. However, diode 824 clamps the negative-going spikes as shown at 826 in FIG. 29d, and only the positive-going spikes 828 trigger transistor 830 "on" (to conduct current for about 50 nanoseconds only, for example), thereby discharging capacitor 832 to develop the "re-trace" part 834 (FIG. 29e) of the waveform 836 appearing at line 839. In between spikes 828, capacitor 832 recharges along ramp 848 as determined by the R-C time constant (as set by resistor 850 and resistor 852).

Transistor 838 amplifies the current available from R-C combination (850, 852, 832) so that waveform 836 drives comparator stage 854 without becoming appreciably distorted. Meanwhile, the video signal at video input 856 (as amplified by transistor 858) sets a reference level $V_2$ (FIG. 29e) which determines where along the waveform 836 the comparator 854 "trips". When such "tripping" occurs, waveform 860 (FIG. 29f) results. Of course, the reference level $V_2$ is always changing as it represents video information received from the patient or specimen.

Transistor 874 shifts the DC voltage levels back down to the usual logic levels (in the present example, zero volts corresponds to "off", and plus five volts corresponds to "on"), and diodes 876 and 878 clamp the "off" and "on" voltage swing limits (zero volts and plus five volts), and transistor 880 is the line driver that feeds the variable width pulses 860 to terminal 882 and the storage oscilloscope 138 (not shown in this view) through about ten feet, for example, of coaxial line. Diode 884 sets the reference voltage level that determines the height of pulses 860. The width of these pulses 860 varies from about 0% (all off — black level) through about 50% (one-half on — middle grey) to 100% (always on — full white). In this specific example, it will be appreciated that there are only six quantized permissible steps as described above in connection with the tomographic function generator and the staircase generator.

Figure 30:
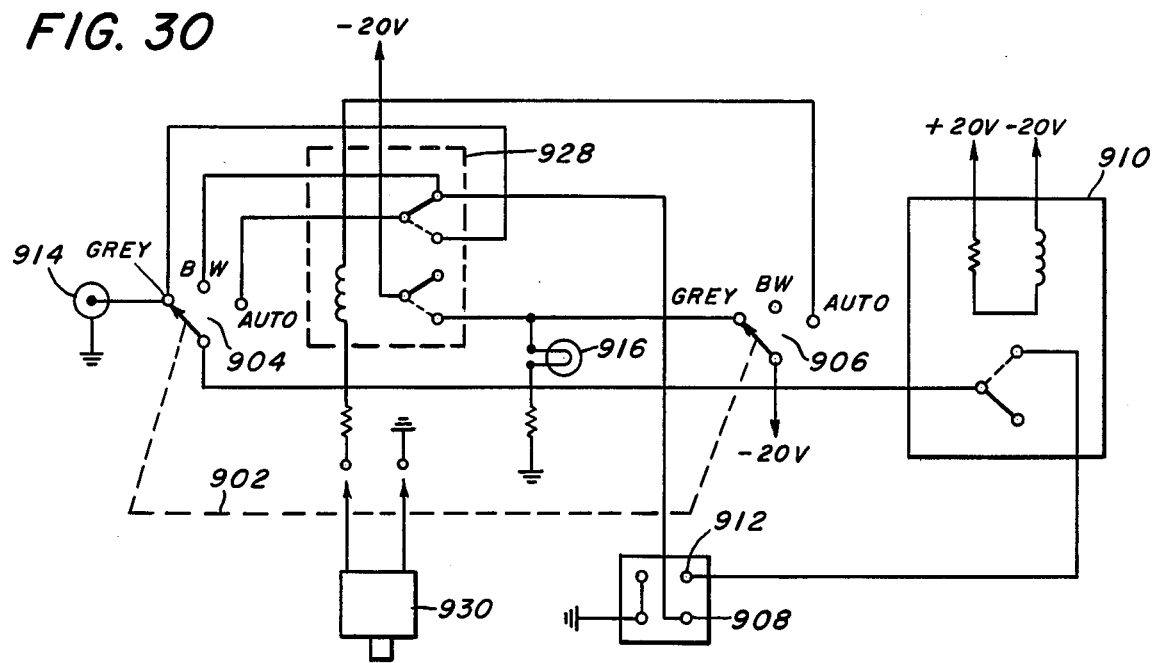
FIG. 30 illustrates schematically a circuit diagram of a form of control switch which enables the operator to switch from conventional bistable to grey-level display.

Referring now to FIG. 30, there is shown a schematic of a form of video switch control module which is suitable for use as video switch 166 of FIG. 16. Switch 902 consists of two gangs 904, 906. When switch 902 is set in the black-and-white position (bistable position), signals at contact 908 from the ultrasonoscope 90 (not shown in this view) pass through switch 902 to relay 910. If both power supplies are functioning (+20 volts DC and −20 volts DC, for example), relay 910 closes and video signals appear at contact 912 and the oscilloscope is activated. However, if either power supply is not functioning, relay 910 remains open, thus preventing any video displays from appearing on the oscilloscope screen. Protection, as offered by relay 910, is preferred in order to prevent video intensities from being displayed on the storage oscilloscope screen if the deflection inputs (X-Y) are not working. For instance, a bright stationary dot might damage the phosphor coating on the oscilloscope screen.

When switch 902 is set to the "grey-level" position, the video input 914 receives grey-level information from the dot-packing module (not shown in this view) which is routed to the oscilloscope terminal 912. Information from terminal 908 is not used. A 12-volt indicator lamp 916 comes on indicating that the grey-level system is in use.

When switch 902 is set into the automatic position, relay 928 governs whether bistable (black and white) or grey information is displayed by being made available at terminal 912. Relay 928 is controlled by push button 930 (168 in FIG. 16) which is of the type that remains latched in either the open or closed position, alternating positions each time button 930 is pushed by the physician or other ultrasonographer. Button 930 is normally mounted close to the patient's or specimen's support position as in the case of the patient stretcher, for example.

Reference will now be made to FIGS. 31a, 31b, 31c, wherein there is illustrated a gate-marker module system such as that shown as element 204 in FIG. 16. Gate pulse 932 (FIG. 31b) is introduced into the gate-marker module system through gate input 934, and it turns transistor 936 on, thereby creating waveform 938 (FIG. 31c) that has an initial negativegoing edge 940. When applied to R-C combination including capacitor 942 and resistor 944, leading edge 940 causes the spike waveform 946 (FIG. 31e) that lasts for approximately three microseconds in this example. Spike waveform 946 turns transistor 958 off for approximately three microseconds, thereby causing the "gate start" marker waveform 960 (FIG. 31g) to appear.

Waveform 938 (FIG. 31c) also drives transistor 962 whose output 964 (FIG. 31d) contains a negative-going edge 966 at the end of the gate pulse 932. Gate pulse 932 is not used directly in the preferred form because the reshaped pulse 964 has a much sharper falling or trailing edge. When applied to R-C combination 968, 970, waveform 964 produces spiked waveform 972 (FIG. 31f). When waveform 972 is applied to transistor 974, the "gate stop output" waveform 976 (FIG. 31h) is produced. It will, therefore, be appeciated that in this fashion the gate start waveform 960 and gate stop waveform 976 are produced.

Figure 32:
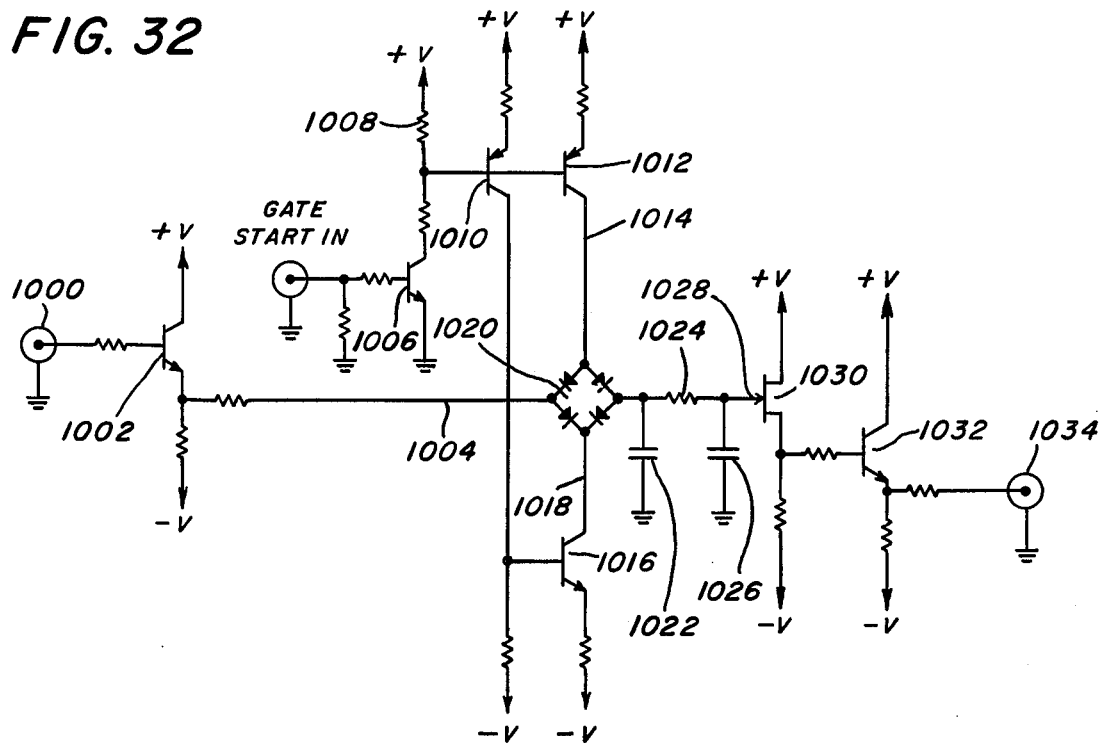
FIG. 32 illustrates schematically a form of circuit diagram of a coordinate catcher adapted for use in the present invention.

Reference is now made to FIG. 32, wherein there is shown a coordinate catcher of the type which might be used as element 200 or 202 in FIG. 16. The X-deflection signal, which is introduced into input 1000, is amplified by emitter-follower transistor 1002 and made available on lead 1004. Meanwhile, the gate start (three microseconds, in this example) pulse turns on transistor 1006 and dropping voltage at resistor 1008 turns on both constant current transistors 1010, 1012. Currents at collector 1014 and from current source transistor 1016 become activated only during the gate start pulse. Both currents 1014, 1018 pull diamond gate 1020 diodes into conduction. X-deflection signals appearing at point 1004 may then pass through the diamond gate 1020 to charge the capacitor 1022. At times in between the gate start pulses, capacitor 1022 stores its previous charge and voltage across the capacitor changes in small steps only during the gate start pulses. Resistor 1024 and capacitor 1026 average such steps into smoothly changing voltages at junction 1028, and these voltages at 1028 represent the continuously changing X-component of the X-deflection signal. Transistors 1030, 1032 amplify voltages at 1028 to provide coordinate position information at X-begin output terminal 1034. Transistor 1030 is preferably a field-effect transistor in order to avoid discharging capacitors 1022, 1026.

With respect to the stop signal, the circuit of FIG. 32 may be duplicated with the gate input 1000 receiving the gate stop input and the output 1034 emitting the X-end output signal. The output represents the X-component of the end of the X-deflection signal. A duplicate set of coordinate catcher modules would be employed so that in total there would be an X-start, X-stop, Y-start, Y-stop coordinate signal-handling capability, and the velocity information is calculated from all four signals.

Figure 33:
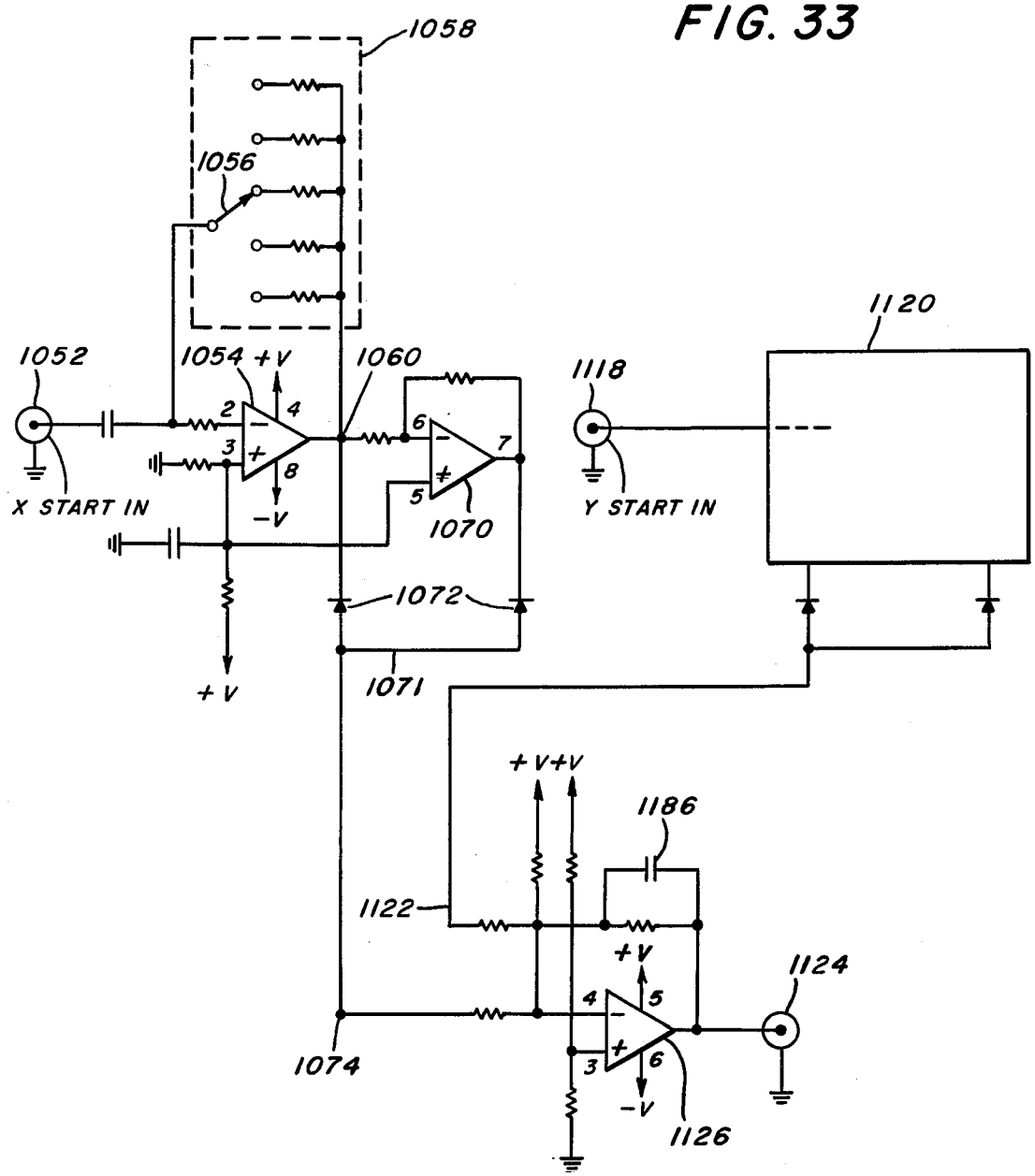
FIG. 33 illustrates schematically a circuit diagram of a form of coordinate velocity calculator adapted for use in the present invention.

Referring now to FIG. 33, there is shown a form of coordinate velocity calculator schematic which is suitable for use as element 232 in FIG. 16. The coordinate velocity catcher calculates the sum of the change in the X-start position against the time plus the change in the Y-start position against time. A second module calculates the sum for the X and Y stopping values. The collective stop and start velocities are what programs the dynamic time-controlled gain module (indicated by reference number 240 in FIG. 16), which corrects the writing intensities on the storage oscilloscope.

The X-start signal enters through input 1052 (from coordinate catcher) and is differentiated by operational amplifier differentiator 1054, well known in the art of analog computers. Selector switch 1056 and resistor network 1058 allow selection of the sensitivity of velocity detection. The velocity signal at junction 1060 is inverted by the operational amplifier 1070 and the two phase-opposed outputs at 1060, 1071 operate the full wave rectifier 1072, whose output at junction 1074 is only negative-going and represents (from about a zero to −10 volt range, in this example) the magnitude only and not the positive or negative sense of the velocity of the X-start coordinate.

The same derivation of velocity is applied by means of a duplicate circuit of 1120 for the Y coordinate as was shown in connection with the X coordinate. The Y-start coordinate input is indicated generally by the number 1118. The magnitude of the Y-start velocity at line 1122 is added to the magnitude of the X-start velocity at 1074 to yield the summation of start velocity output 1124, due to operational amplifier 1126. Capacitor 1186 is employed to smooth out irregular waveforms and convert them into smoothly changing voltage output 1124 which is preferable in order to optimally program the dynamic time-controlled gain module. Similarly, a second velocity catcher module is used to calculate the summated stop velocity. The summated stop velocity is also used to program the dynamic time-controlled gain module.

Referring now to FIGS. 34, 34a, 34b, 34c and 34d, it is noted that the gate input 1210 is amplified by transistor 1212 to produce pulse 1214, which turns off clamp transistors 1216, 1218. (The letters "A", "B", "C", "D" and "E" represent connections to similarly labeled circuit portions.) Transistors 1216, 1218 reset integrating operational amplifiers 1220, 1222. Amplifier 1220 produces ramp waveform 1230 (FIG. 34c) whose maximum height 1232 is proportional to the start velocity signal received at start velocity input 1234. Lead 1236 transfers the start velocity signal through resistor 1238 only when gate input 1210 is on, owing to the gate circuit 1211. Point 1240 adds a positive offset voltage 1250 (FIG. 34d) to raise ramp 1230 upwards to ramp 1252. Thus, the leading edge height 1254 depends upon the start velocity signal.

A similar sequence of events occurs at amplifier 1222 to produce ramp 1270 that has trailing edge heights 1272 depending upon the stop-velocity signal at stop-velocity input 1274. Ramp signal 1270 is fed through resistor 1302 into amplifier 1304 so that the output waveform 1306 is trapezoidal and has leading and trailing edges 1308, 1310, respectively, dependent upon starting and stopping velocities, respectively. This trapezoidal waveform is supplied into the storage oscilloscope in such fashion that writing intensity increases with lateral motion of the time-axis line. As the lateral motion may be arcuate or otherwise non-cartesian, waveform 1306 is programmed in such fashion as to handle a wide variety of lateral manipulative motions of the display time-axis line on the storage oscilloscope.

Figure 35:
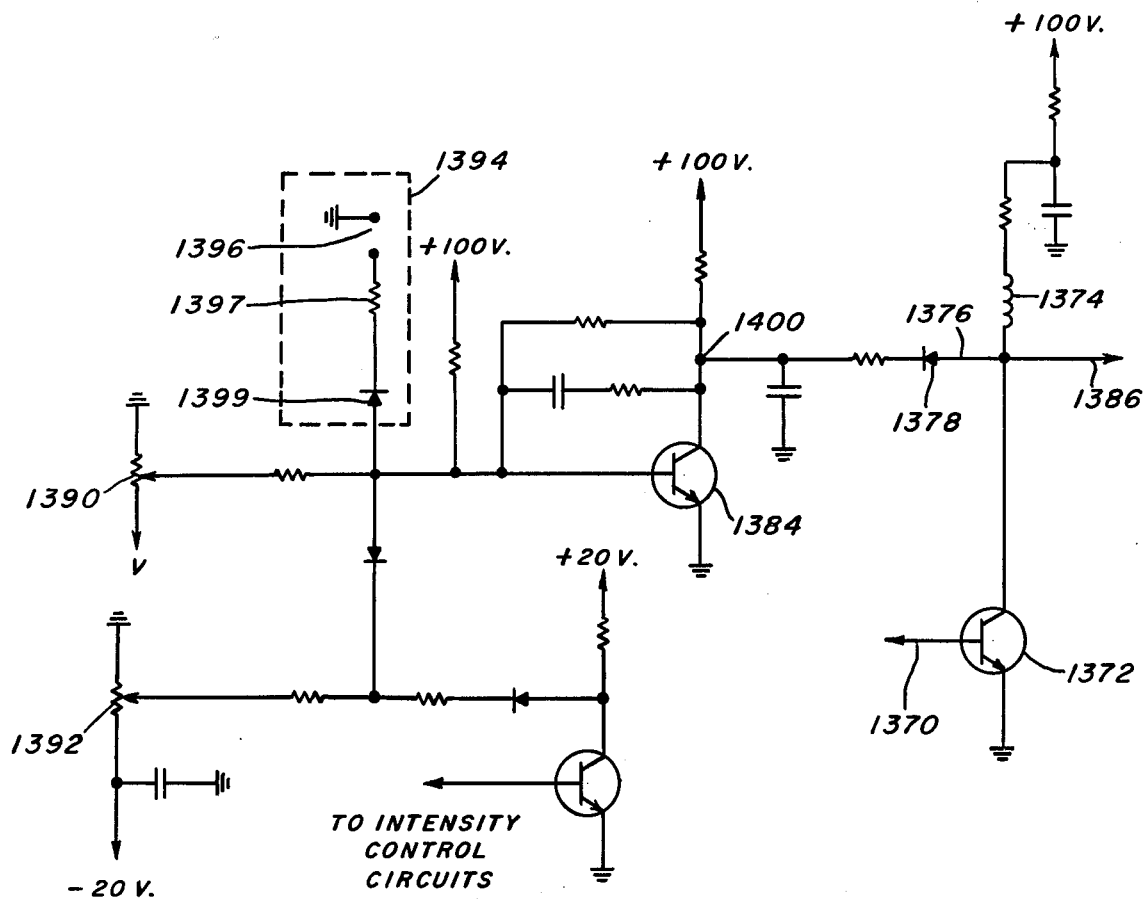
FIG. 35 illustrates schematically a modified circuit diagram of a form of interface with a storage oscilloscope suitable for use with the present invention.

Referring now to FIG. 35, there is shown a portion of a conventional Z-axis circuit of a storage oscilloscope with certain modifications. Video signals from the dot-packing module (element 152 in FIG. 16) travel through the Z-axis circuitry of the storage oscilloscope until such signals enter input line 1370 and key the transistor 1372 to either an "on" or "off" position. During the turn off of transistor 1372, inductor 1374 "kicks" upwards in voltage until such voltage at lead 1376 is clamped by diode 1378. Reference voltages applied by transistor 1384 determine the entire clamping action (from +10 to +100 volts, in this example) and hence the writing intensity to the storage oscilloscope screen as delivered to additional circuitry through lead 1386.

Several factors employing the voltage referring action of transistor 1384 including write-through intensity potentiometer 1390 (through a control which conveniently may be mounted on the front panel of the storage oscilloscope), writing intensity potentiometer 1392 and a modification of the present invention contained within the dotted enclosure labeled 1394, which modification allows external augmentation of the writing intensity by way of external voltage input controls applied at terminal 1396. Negative-going voltages at 1396 from the dynamic time-controlled gain module decrease the base current in transistor 1384 causing reference voltage at 1400 to increase. Such increasing voltages at 1400 open up the clamping voltage reference at diode 1378, thereby allowing higher writing intensity to occur on the storage oscilloscope screen, in proportion to the trapezoidal time varying velocity of the lateral time-axis scanning motion. During normal operation of transistor 1384, the base remains at 0.7 volts above ground, for example. If negative-going control voltages ranging from zero to −20 volts are applied to point 1396, resistor 1397 conducts zero to −4 mA, and the transistor 1384 responds by increasing voltage at 1400 from +10 to +90 volts. Diode 1399 is provided to protect transistor 1384 from burnouts due to accidental reversals of voltages applied at 1396.

EXAMPLE

In order to provide an illustrative example as to the specific operation of the preferred embodiment of the system and method of the present invention, the following specific application will be considered. Considering an example wherein six discrete levels would be employed in a grey-level system, and assuming the sonic range to have outer limits of about 15 to 25 dB dynamic range, six is a desirable number of grey levels for display on a storage oscilloscope. Typically, ultrasound signals monitored emerging from the ultrasonoscope will have a range of about 1.0 to about 5.0 MHz and last for a duration of the first 100 to first 300 microseconds after the main pulse from transducer 92 (FIG. 16). These 100 to 300 microsecond durations repeat about every 1.0 millisecond, and this 1.0 millisecond interval is determined by the ultrasonoscope 90. Amplitudes of the ultrasound signals as monitored emerging from the ultrasonoscope 90 range from about eight millivolts peak-to-peak to about 800 millivolts peak-to-peak. A typical viewable signal might be about 250 millivolts peak-to-peak at a frequency of about 2.25 MHz, for example. Once processed by amplifier 100, the signal emerging therefrom has been increased to a maximum amplitude of about 5.0 volts peak-to-peak with a typical viewing amplitude for the middle grey imaging level being about 1.3 to 2.0 volts peak-to-peak. The output voltage signal 120 emerging from linear receiver 112 is directly proportional to the peak-to-peak amplitude of input signal 106 which it receives. For signals 106 ranging from about 1.0 to 5.0 volts peak-to-peak (positive and negative going) the voltage signal 120 ranges from about 1.0 volts DC to about 5.0 volts DC positive going only.

As has been mentioned, gate signal 118 determines the active time of linear receiver 112 and the entire grey-level system. The master gate timer 116 may set the length of gate pulse in a range of about 200 to 400 microseconds, typically about 300 microseconds. The gate pulse 118 is initiated at the time the external gate pulse 114 from the ultrasonoscope 90A begins its "on" condition, which condition is typically represented by transition from zero volts DC to about +15 volts DC, and the "on" condition is maintained for the first 500 microseconds after the transducer 92 emits its ultrasonic wave or "main bang".

For receiver signals 120 ranging from 1.25, 2.5, 5.0 volts DC, the tomographic function generator 128 produces outputs of 0.8, 2.4, and 4.0 volts DC at 130, respectively, for typical slide potentiometer settings. In this example, the tomographic function generator 128 will have only six possible output states ranging from 0.0 volts DC to 4.0 volts DC along specific discrete steps of 0.0, 0.8, 1.6, 2.4, 3.2 and 4.0 volts DC. These six outputs may be displayed as shades of grey in the fashion to be described herein on a suitable storage oscilloscope, such as that sold under the trademark Tektronix 611.

The phase-synchronous tone-burst generator 160 emits a signal 162 in the fashion described above, to the dot-packing module 152. The synchronous tone signals 162 may range from about 0.5 MHz to 1.0 MHz with typical tones commonly used being about 650 KHz (0.65 MHz) and 850 KHz (0.85 MHz) depending upon the degree of magnification selected for the imaging process. The tone-burst signals are sinusoidal, 5.0 volts peak-to-peak, and lasting about 300 microseconds and recurring every 1.04 millisecond.

The dot-packing module 152 is driven by the tone-burst 162 and stepwise variable patient information at 150. In the dot-packing module 152, 0.0, 0.8, 1.6, 2.4, 3.2 and 4.0 volts produce the squarish output pulses 164 whose "on-time" duty factor is discretely variable at 0%, 20%, 40%, 60%, 80% and 100%, respectively, as commanded by the signals at 150. The output pulses 164 are −0.64 volts in the "off" stage and +5.0 volts in the "on" stage. The Z-axis threshold of the storage oscilloscope 138 is internally adjusted to store signals on the scope screen whenever the Z-input signal 176 exceeds +0.75 volts DC.

Referring now to the means for compensating for variations in speed of sweep of the transducer, the waveforms 196, 198 which are introduced into the coordinate catchers 200, 202, respectively, recur at about 1.04 millisecond and have a sawtooth shape with peak-to-peak voltage amplitudes ranging from about zero to six volts peak-to-peak with typical amplitudes of about three volts peak-to-peak. With regard to the coordinate catchers 200, 202, the signal to initiate operation may be created in the following fashion. The 300 microsecond gate signal 118 from gate timer 116 drive the gate marker module 204. The gate marker module 204 provides a short trigger pulse 206 that corresponds to the starting edge of gate pulse 118 and also a short trigger pulse 208 that corresponds to the stopping edge of the gate pulse 118. This serves to provide both the top and bottom limits of the time axis. Pulses 206, 208 are positive going, 5.0 volts peak-to-peak and last about 3.0 microseconds.

Referring now to the dynamic time-controlled gain module 240, the voltage signals 230, 234 may range from about zero to +10 volts DC when they are applied in concert with the gate pulse 118 to dynamic time-controlled gain module 240 to produce a waveform 242. Waveform 242 ranges from about zero to −18 volts peak-to-peak and is fed into the interface circuitry 244 of the storage oscilloscope. While it is believed that one skilled in the art would have no difficulty in practicing the present invention without the benefit of the present example, it is believed that the present example will enhance the understanding of the specific means in which the best mode of the present invention may be practiced.

It will, therefore, be appreciated that the present invention provides a reliable, economically practical ultrasonic display system wherein an electrical signal which is related to a reflected ultrasonic signal returned from a patient or other specimen is processed in such fashion that grey-level display may be provided on a storage oscilloscope. All of this is accomplished in such fashion as to permit adoption of this system without requiring large capital investment in specially designed ultrasonoscopes and storage oscilloscopes. In addition to providing for a range of predetermined grey levels for use in the displays, the present system, in its preferred embodiment, also provides means for compensating for variations in speed of movement of the ultrasonic transducer over the test specimen. As a result, one may advantageously and economically obtain the benefits of improved data resulting from grey-level imaging as distinguished from bistable imaging while otherwise employing conventional ultrasonography techniques and basic equipment. If desired, all of this may be accomplished while permitting switching from bistable to grey-level imaging and vice versa in a particular installation.

Variations in the specific schematic diagrams and circuit diagrams as shown herein will occur to those skilled in the art and may advantageously be adopted without departing from the present invention and the best mode of practicing the same as disclosed herein. While not specifically illustrated, it will be appreciated that the electronic processing means, schematically illustrated in FIG. 16 and in the related drawings, may advantageously be housed within a single unit which may be electrically connected to ultrasonoscope 90 and storage oscilloscope 138. In this fashion, the conversion unit may be prepackaged as a single entity except for such minor circuit revisions as might be made in the ultrasonoscope 90 and storage oscilloscope 138. Also, if the test features provided by staircase generator 140 (FIG. 16) are not desired, this element may be eliminated with lead 130 being connected directly to dot-packing module 152 and the gate signal lead 144 being eliminated. Further, while for convenience of disclosure, specific reference has been made herein to advantageous use in connection with a storage oscilloscope, it will be appreciated that many advantages of the invention may be obtained in connection with the use of other types of data receiving means, such as other recording or display systems. Among examples of such alternate means are (a) a cathode-ray tube employed in combination with time exposure photographic equipment and (b) a facsimile receiving unit, such as those employing electrically sensitive paper.

While for purposes of clarity of illustration, specific reference has been made herein to phase-synchronous tone-burst generators, it will be appreciated that a tone-burst generator having a programmed slew rate phase change may be employed to produce a complex, fine-grained dot pattern as a refinement in grey-level operation.

Whereas, particular embodiments of the invention have been described above for purposes of illustration, it will be evident to those skilled in the art that numerous variations of the details may be made without departing from the invention as defined in the appended claims.

I claim:

1. A grey-level ultrasonic imaging system comprising:
   ultrasonic test means for generating an ultrasonic wave, impinging said ultrasonic wave upon a test specimen, receiving acoustical waves from said test specimen and converting said acoustical waves into electrical signals,
   amplifier means for amplifying said electrical signals,
   linear receiver means for receiving said amplified signals and emitting positive voltage signals proportional to said amplified signals,
   gating means controlling the operating times of said linear receiver,
   signal converting means for converting said positive voltage signals into non-linear function signals,
   dot-packing module means for receiving said non-linear function signals from said signal converting means,
   tone-burst generator means for delivering tone-burst generator signals to said dot-packing module means,
   said dot-packing module means producing modulated dot width output terminals with spacing between the dots being controlled by said tone-burst generator signals and the width of said modulated dots controlled by said non-linear function signals with said dot widths being generally proportional to the amplitude of said non-linear function signals, and
   data receiving means for receiving said modulated dot width output signals, whereby said data receiving means may record or display said modulated dot width output signals.

2. The grey-level ultrasonic imaging system of claim 1 including:
   said ultrasonic test means receiving said acoustical waves from said test specimen by reflection from said test specimen.

3. The grey-level ultrasonic imaging system of claim 2 including:
   said data receiving means including storage oscilloscope means for visually displaying said modulated dot width output signals.

4. The grey-level ultrasonic imaging system of claim 3 including:
   said signal converting means including function generator means for converting said positive voltage signals into logarithmic functions thereof.

5. The grey-level ultrasonic imaging system of claim 4 including:
   said signal converting means including contrast control means for establishing discrete levels of output responsive to signals from said function generator means.

6. The grey-level ultrasonic imaging system of claim 5 including:
   said contrast control means including adjustable potentiometer means associated with said function generator means, and
   said adjustable potentiometer means having about six to ten output levels, whereby about six to ten grey levels will be visualized.

7. The grey-level ultrasonic imaging system of claim 5 including:
   said gating means controlling the operation of said tone-burst generator means.

8. The grey-level ultrasonic imaging system of claim 7 including:
   said gating means including a master gate timer operatively associated with said linear receiver means and said tone-burst generator means.

9. The grey-level ultrasonic imaging system of claim 5 including:
   said contrast control means having output levels equal in number to the number of visual display levels of said system.

10. The grey-level ultrasonic imaging system of claim 8 including:
    staircase test generator means for testing said system,
    said staircase generator means in a first mode operatively associated with said master gate timer to receive gating pulse signals and initiate a responsive ladder-like voltage test wave to said dot-packing module means, and
    said staircase generator means in a second mode permitting passage of signals from said signal converting means to said dot-packing module means.

11. The grey-level ultrasonic imaging system of claim 9 including:
    said modulated dot width output signals of said dot-packing module means being stepwise variable corresponding to said output levels.

12. The grey-level ultrasonic imaging system of claim 11 including:
    video switch control means for permitting operation of said system in a grey-level mode or a bistable mode.

13. The grey-level ultrasonic imaging system of claim 11 including:
    said tone-burst generator means including means for emitting tone-burst generator signals which are sinusoidal waveforms.

14. The grey-level ultrasonic imaging system of claim 13 including:
    said tone-burst generator means emitting said tone-burst generator signals responsive to receipt of signals from said gating means.

15. The grey-level ultrasonic imaging system of claim 13 including:
    said tone-burst generator means being a phasesynchronous tone-burst generator.

16. The grey-level ultrasonic imaging system of claim 15 including:
    said storage oscilloscope means having means for storing signals on the screen of said oscilloscope whenever a Z-input signal exceeds a predetermined voltage level.

17. The grey-level ultrasonic imaging system of claim 3 including:
    transducer speed compensating means for compensating for variations in the speed of physical movement of said transducer, whereby blending between successively generated time axes will be effected substantially smoothly.

18. The grey-level ultrasonic imaging system of claim 17 including:
said ultrasonic test means having interface circuitry means for emitting X-deflection voltage signals and Y-deflection voltage signals for time axis line display and orientation on said storage oscilloscope means, and
said transducer speed compensating means being interposed between said ultrasonic test means and said storage oscilloscope means.

19. The grey-level ultrasonic imaging system of claim 18 including:
said gating means providing start and stop signals to said transducer speed compensating means indicating, respectively, the initiation and termination of gating signals.

20. The grey-level ultrasonic imaging system of claim 19 including:
said gating means including gate marker means for receiving said gating signals and emitting responsive signals to said speed compensating means indicating said initiation and termination of said gating signals.

21. The grey-level ultrasonic imaging system of claim 20 including:
said transducer speed compensating means including first coordinate catcher means, second coordinate catcher means, first coordinate velocity calculator means, second coordinate velocity calculator means and time-controlled gain module means,
said first coordinate catcher means adapted to receive said X-deflection voltage signals and responsive to receipt of said start and stop signals from said gating means emitting, respectively, X-start voltage signals to said first coordinate velocity calculator means and X-stop voltage signals to said second coordinate velocity calculator means,
said second coordinate catcher means adapted to receive said Y-deflection voltage signals and responsive to receipt of said start and stop signals from said gating means emitting, respectively, Y-start voltage signals to said first coordinate velocity calculator means and Y-stop voltage signals to said second coordinate velocity calculator means,
said first coordinate velocity calculator means responsive to receipt of said X-start voltage signals and Y-start voltage signals adapted to emit start velocity voltage signals to said time-controlled gain module means,
said second coordinate velocity calculator means responsive to receipt of said X-stop voltage signals and Y-stop voltage signals adapted to emit stop velocity voltage signals to said time-controlled gain module means,
said gating means for applying said gating signals to said time-controlled gain module means, and
said time-controlled gain module means responsive to receipt of said start velocity voltage signals, said stop velocity voltage signals and said gating signals adapted to emit a speed compensating signal to said storage oscilloscope means.

22. A grey-level ultrasonic imaging apparatus comprising:
amplifier means for amplifying electrical signals which are related to acoustical waves received by an ultrasonoscope from a test specimen,
linear receiver means for receiving said amplified signals and emitting positive voltage signals proportional to said amplified signals,
gating means controlling the operating times of said linear receiver,
signal converting means for converting said positive voltage signals into non-linear function signals,
dot-packing module means for receiving said non-linear function signals from said signal converting means,
tone-burst generator means for delivering tone-burst generator signals to said dot-packing module means, and
said dot-packing module means producing modulated dot width output signals with spacing between said dots being controlled by said tone-burst generator signals and the width of said modulated dots controlled by said non-linear function signals with said dot widths being generally proportional to the amplitude of said non-linear function signals, whereby delivery of said modulated dot width output signals to data receiving means will permit display or recording of said modulated dot width output signals.

23. The grey-level ultrasonic imaging system of claim 22 including:
said signal converting means including function generator means for converting said positive voltage signals into logarithmic functions thereof.

24. The grey-level ultrasonic imaging system of claim 23 including:
said signal converting means including contrast control means for establishing discrete levels of output responsive to signals from said function generator means.

25. The grey-level ultrasonic imaging system of claim 24 including:
said contrast control means including adjustable potentiometer means associated with said function generator means, and
said adjustable potentiometer means having about six to ten output levels, whereby about six to ten grey levels will be visualized.

26. The grey-level ultrasonic imaging system of claim 24 including:
said gating means controlling the operation of said tone-burst generator means.

27. The grey-level ultrasonic imaging system of claim 26 including:
said gating means including a master gate timer operatively associated with said linear receiver means and said tone-burst generator means.

28. The grey-level ultrasonic imaging system of claim 24 including:
said contrast control means having output levels equal in number to the number of visual display levels of said system.

29. The grey-level ultrasonic imaging system of claim 27 including:
staircase test generator means for testing said system,
said staircase generator means in a first mode operatively associated with said master gate timer to receive gating pulse signals and initiate a responsive ladder-like voltage test wave to said dot-packing module means, and
said staircase generator means in a second mode permitting passage of signals from said signal converting means to said dot-packing module means.

30. The grey-level ultrasonic imaging system of claim 28 including:
said modulated dot width output signals of said dot-packing module means being stepwise variable corresponding to said output levels.

31. The grey-level ultrasonic imaging system of claim 30 including:
video switch control means for permitting operation of said system in either a grey-level mode or a bistable mode.

32. The grey-level ultrasonic imaging system of claim 30 including:
said tone-burst generator means including means for emitting tone-burst generator signals which are sinusoidal waveforms.

33. The grey-level ultrasonic imaging system of claim 32 including:
said tone-burst generator means emitting said tone-burst generator signals responsive to receipt of signals from said gating means.

34. The grey-level ultrasonic imaging system of claim 33 including:
said tone-burst generator means being a phase-synchronous tone-burst generator.

35. The grey-level ultrasonic imaging system of claim 22 including:
transducer speed compensating means for compensating for variations in the speed of physical movement of said transducer, whereby blending between successively generated time axes will be effected substantially smoothly.

36. The grey-level ultrasonic imaging system of claim 35 including:
interface circuitry means for emitting X-deflection voltage signals and Y-deflection voltage signals for time axis line display and orientation on a storage oscilloscope.

37. The grey-level ultrasonic imaging system of claim 36 including:
said gating means for providing start and stop signals to said transducer speed compensating means indicating the initiation and termination, respectively, of gating signals.

38. The grey-level ultrasonic imaging system of claim 37 including:
said gating means including gate marker means for receiving said gating signals and emitting responsive signals to said speed compensating means indicating said initiation and termination of said gating signals.

39. The grey-level ultrasonic imaging system of claim 38 including:
said transducer speed compensating means including first coordinate catcher means, second coordinate catcher means, first coordinate velocity calculator means, second coordinate velocity calculator means and time-controlled gain module means,
said first coordinate catcher means adapted to receive said X-deflection voltage signals and responsive to receipt of said start and stop signals from said gating means emitting, respectively, X-start voltage signals to said first coordinate velocity calculator means and X-stop voltage signals to said second coordinate velocity calculator means,
said second coordinate catcher means adapted to receive said Y-deflection voltage signals and responsive to receipt of said start and stop signals from said gating means emitting, respectively, Y-start voltage signals to said first coordinate velocity calculator means and Y-stop voltage signals to said second coordinate velocity calculator means,
said first coordinate velocity calculator means responsive to receipt of said X-start voltage signals and Y-start voltage signals adapted to emit start velocity voltage signals to said time-controlled gain module means,
said second coordinate velocity calculator means responsive to receipt of said X-stop voltage signals and Y-stop voltage signals adapted to emit stop velocity voltage signals to said time-controlled gain module means,
said gating means adapted to apply said gating signals to said time-controlled gain module means, and
said time-controlled gain module means responsive to receipt of said start velocity voltage signals, and stop velocity voltage signals and said gating signals adapted to emit a speed compensating signal.

40. A method of ultrasonic grey-level imaging comprising:
amplifying electrical signals which are related to acoustical waves received by an ultrasonoscope from a test specimen,
converting said amplified electrical signals to positive voltage signals monotonically related to said amplified electrical signals,
converting said positive voltage signals to non-linear function signals,
producing modulated dot width output signals having dot widths generally proportional to the amplitude of said non-linear function signals,
controlling the spacing between said dots by tone-burst generator signals, and
displaying said modulated dot width output signals.

41. The method of ultrasonic grey-level imaging of claim 40 including:
producing said non-linear function signals as logarithmic functions of said positive voltage signals.

42. The method of ultrasonic grey-level imaging of claim 41 including:
producing discrete levels of output of said logarithmic function signals.

43. The method of ultrasonic grey-level imaging of claim 42 including:
producing said logarithmic function signals in about six to ten levels corresponding to a like number of grey levels to be visualized.

44. The method of ultrasonic grey-level imaging of claim 43 including:
providing gating signals to the means converting said amplified electrical signals into said positive voltage signals and to the means generating said tone-burst generator signals.

45. The method of ultrasonic grey-level imaging of claim 44 including:
compensating for variations in sweep speed of scanning movement of the transducer by providing velocity compensating signals to the image displaying means.

46. The method of ultrasonic grey-level imaging of claim 45 including:
providing said gating signals to the means for compensating for variations in speed of scanning movement,
employing said gating signals to create starting trigger pulses and stopping trigger pulses coincident with the beginning and ending, respectively, of said gating signals, circuit means responsive to said starting trigger pulses and said stopping trigger pulses for monitoring the initiation and termination of X and Y transducer position signals, calculating the initial and terminal velocities of scanning from said position signals, and delivering to said display means trapezoidal composite waveforms related to said voltage signals.

47. The method of ultrasonic grey-level imaging of claim 46 including:

providing said display means with means for displaying grey-level, non-cartesian scanning raster formats, whereby said trapezoidal composite waveforms control uniformity of grey-level imaging in non-cartesian scan formats to compensate for changes in sweep velocity of transducer scans.

* * * * *